(12) United States Patent
Awiszus et al.

(10) Patent No.: US 12,168,150 B2
(45) Date of Patent: *Dec. 17, 2024

(54) PERSONAL PROTECTIVE EQUIPMENT SAFETY SYSTEM USING CONTEXTUAL INFORMATION FROM INDUSTRIAL CONTROL SYSTEMS

(71) Applicant: 3M INNOVATIVE PROPERTIES COMPANY, St. Paul, MN (US)

(72) Inventors: Steven T. Awiszus, Woodbury, MN (US); Michael G. Wurm, Waukesha, WI (US); David R. Stein, White Bear Lake, MN (US); Johannes P. M. Kusters, Austin, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 1015 days.

This patent is subject to a terminal disclaimer.

(21) Appl. No.: 17/250,232

(22) PCT Filed: Jun. 21, 2019

(86) PCT No.: PCT/IB2019/055262
§ 371 (c)(1),
(2) Date: Dec. 21, 2020

(87) PCT Pub. No.: WO2019/244125
PCT Pub. Date: Dec. 26, 2019

(65) Prior Publication Data
US 2021/0210202 A1 Jul. 8, 2021

Related U.S. Application Data

(60) Provisional application No. 62/688,942, filed on Jun. 22, 2018.

(51) Int. Cl.
*G05B 19/042* (2006.01)
*A62B 99/00* (2009.01)
(Continued)

(52) U.S. Cl.
CPC .......... *A62B 99/00* (2013.01); *G05B 19/0428* (2013.01); *G06F 18/214* (2023.01);
(Continued)

(58) Field of Classification Search
None
See application file for complete search history.

(56) References Cited

U.S. PATENT DOCUMENTS 11,933,453 B2 * 3/2024 Swift ...................... F16P 3/147
2008/0018472 A1    1/2008 Dasilva
(Continued)

FOREIGN PATENT DOCUMENTS

EP          0533329          3/1993

OTHER PUBLICATIONS

International Search Report for PCT International Application No. PCT/IB2019/055262, mailed on Jan. 10, 2020, 5 pages.

*Primary Examiner* — Curtis A Kuntz
*Assistant Examiner* — Jerold B Murphy
(74) *Attorney, Agent, or Firm* — Sriram Srinivasan; Christopher D. Karlen

(57) ABSTRACT

In some examples, a system includes an article of personal protective equipment (PPE) that includes a communication component; an industrial controller device that is configured to control an industrial device and includes a communication component; and a computing device communicatively coupled to the article of PPE and the industrial controller device, wherein the computing device is configured to: receive PPE data from the article of PPE and industrial controller data from the industrial controller device; deter- (Continued)

mine, based at least in part on a set of the PPE data that temporally corresponds to a set of the industrial controller data, an occurrence of a safety event; and perform, based at least in part on the determination of the safety event, at least one operation.

3 Claims, 5 Drawing Sheets

(51) Int. Cl.
*G06F 18/214* (2023.01)
*G06Q 10/0639* (2023.01)
*G07C 1/10* (2006.01)
*G08B 21/04* (2006.01)
*G16H 40/40* (2018.01)
*G16H 40/67* (2018.01)
*H04Q 9/00* (2006.01)

(52) U.S. Cl.
CPC ......... *G06Q 10/06398* (2013.01); *G07C 1/10* (2013.01); *G08B 21/0438* (2013.01); *G16H 40/40* (2018.01); *G16H 40/67* (2018.01); *H04Q 9/00* (2013.01)

(56) References Cited

U.S. PATENT DOCUMENTS

| | | |
|---|---|---|
| 2015/0284231 A1 | 10/2015 | Grant |
| 2016/0271800 A1 | 9/2016 | Stubbs |
| 2016/0282843 A1* | 9/2016 | Michalscheck .... G05B 19/4185 |
| 2018/0012470 A1* | 1/2018 | Kritzler ................ G06Q 50/265 |
| 2018/0122218 A1 | 5/2018 | Shanley |

\* cited by examiner

PERSONAL PROTECTIVE EQUIPMENT SAFETY SYSTEM USING CONTEXTUAL INFORMATION FROM INDUSTRIAL CONTROL SYSTEMS

CROSS REFERENCE TO RELATED APPLICATIONS

This application is a national stage filing under 35 U.S.C. 371 of PCT/IB2019/055262, filed Jun. 21, 2019, which claims the benefit of U.S. Provisional Application No. 62/688,942, filed Jun. 22, 2018, the disclosure of which is incorporated by reference in its/their entirety herein.

TECHNICAL FIELD

The present disclosure relates to the field of personal protective equipment. More specifically, the present disclosure relates to personal protective equipment that generate data.

BACKGROUND

Personal protective equipment (PPE) may be used to protect a user (e.g., a worker) from harm or injury from a variety of causes in a work environment. For example, fall protection equipment is important safety equipment for workers operating at potentially harmful or even deadly heights. To help ensure safety in the event of a fall, workers often wear safety harnesses connected to support structures with fall protection equipment such as lanyards, energy absorbers, self-retracting lifelines (SRLs), descenders, and the like. As another example, when working in areas where there is known to be, or there is a potential of there being, dusts, fumes, vapors, gases or other contaminants that are potentially hazardous or harmful to health, it is common for a worker to use an air purifying respirator or in some cases, a supplied air respirator. While a large variety of respiratory protection devices are available, some commonly used devices include powered air purifying respirators (PAPR) and a self-contained breathing apparatus (SCBA). Other PPE include those for hearing protection (ear plugs, earmuffs), vision protection (safety spectacles, goggles, welding shields or other face shields), head protection (e.g., helmets, hard hats, or the like), and protective clothing.

SUMMARY

In general, the present disclosure describes systems and techniques for determining safety events based on worker (and PPE) interactions with industrial devices. Industrial devices may pose safety hazards to workers who may not be properly protected by PPE or prepared/trained to interact with the industrials. Examples of industrial devices may include conveyors, drives and drive systems, motors, mixers, reactors, robotic devices, control systems, presses, stamps, heating or cooling elements, light sources, drilling devices, etching, devices, printing devices, ventilation devices, and sensing devices, to name only a few examples. Techniques of this disclosure may apply data fusion techniques to data from industrial devices and data from PPE and workers in order to determine or otherwise identify safety events. Rather than relying solely on data from an industrial device or solely from a worker and/or PPE, techniques of this disclosure may detect safety events based on data from industrial devices that temporally and/or physically proximally correspond to data related to workers and/or PPE. By utilizing such temporal and physical relationships between certain data from industrial devices that temporally correspond to data related to workers and/or PPE, techniques of this disclosure may identify hazardous, dangerous, or unproductive circumstances that arise from insufficient training or protection of the worker existing contemporaneously with operation of an industrial control device.

By identifying or predicting safety events based on data from industrial devices and workers/PPE, techniques of this disclosure may more quickly and accurately identify safety events that may affect the worker's safety, the operation of the articles of PPE, and/or the condition of the work environment to name only a few examples. In some instances, rather than evaluating the cause of a safety event long after the safety event has occurred (and potential harm to the worker has occurred), the techniques of this disclosure may proactively and preemptively generate notifications and/or alter the operation of PPE and/or industrial devices before or immediately when a safety event occurs.

In some examples, a system may include an article of personal protective equipment (PPE) having at least one sensor configured to generate a stream of usage data; and an analytical stream processing component comprising: a communication component that receives the stream of usage data from the at least one sensor of the article of PPE; a memory configured to store at least a portion of the stream of usage data and at least one model for detecting a safety event signature, wherein the at least one model is trained based as least in part on a set of usage data generated, prior to receiving the stream of usage data, by one or more other articles of PPE of a same type as the article of PPE; and one or more computer processors configured to: detect the safety event signature in the stream of usage data based on processing the stream of usage data with the model, and generate an output in response to detecting the safety event signature.

The details of one or more examples of the disclosure are set forth in the accompanying drawings and the description below. Other features, objects, and advantages of the disclosure will be apparent from the description and drawings, and from the claims.

Figure 1:
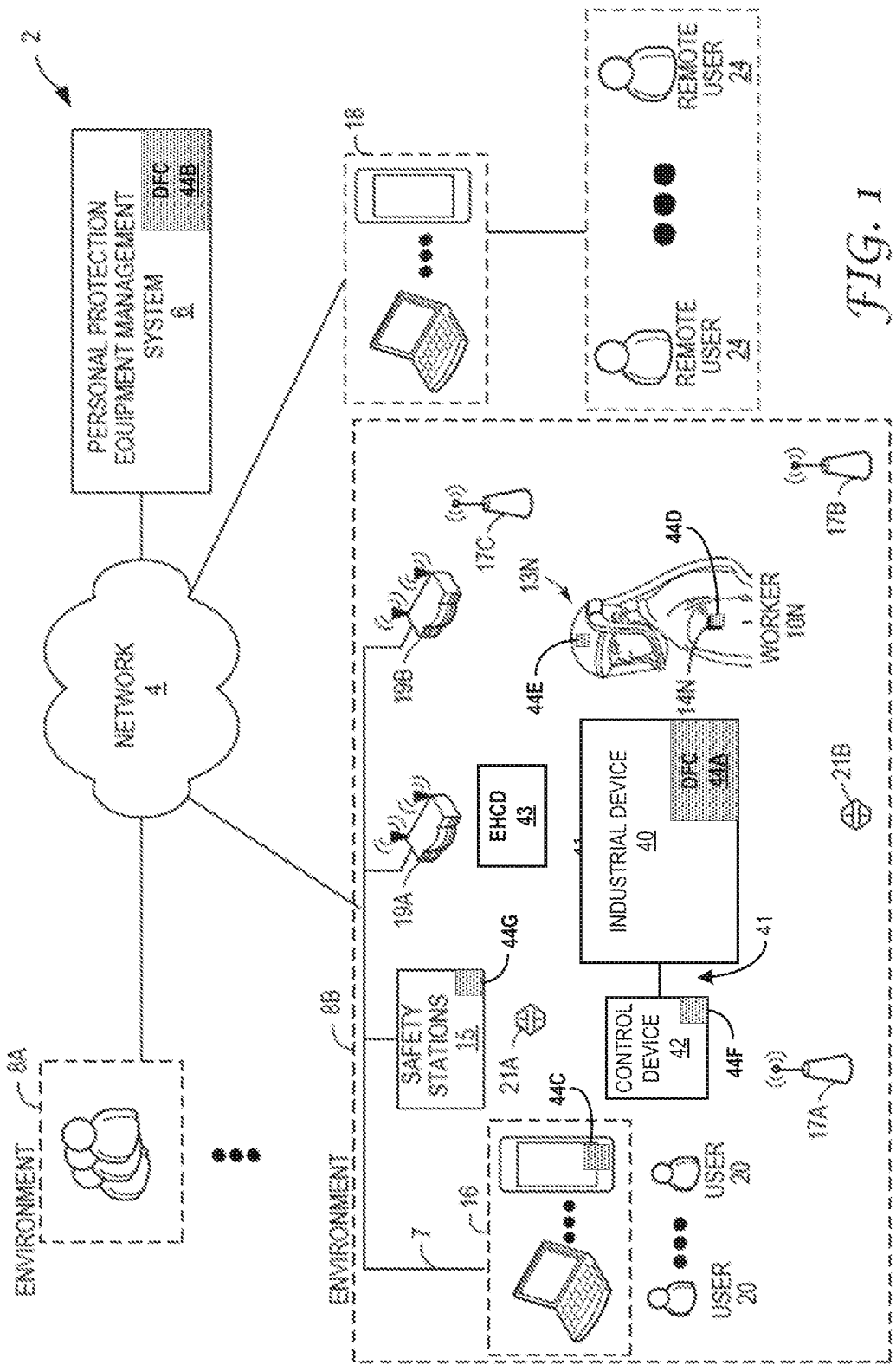
FIG. 1 is a block diagram illustrating an example system in which personal protective equipment (PPEs), such as air purifying systems, having embedded sensors and communication capabilities are utilized within a number of work environments and are managed by a personal protective equipment management system (PPEMS) in accordance with various techniques of this disclosure.

It is to be understood that the embodiments may be utilized and structural changes may be made without departing from the scope of the invention. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

According to aspects of this disclosure, an article of PPE may include sensors for capturing data that is indicative of operation, location, or environmental conditions surrounding an article of PPE. Sensors may include any device that generates data or context information. Such data may generally be referred to herein as usage data or, alternatively, operation data or sensor data. In some examples, usage data may take the form of a stream of samples over a period of time. In some instances, the sensors may be configured to measure operating characteristics of components of the article of PPE, characteristics of a worker using or wearing the article of PPE, and/or environmental factors associated with an environment in which the article of PPE is located. Moreover, as described herein, the article of PPE may be configured to include one or more electronic components for outputting communication to the respective worker, such as speakers, vibration devices, LEDs, buzzers or other devices for outputting alerts, audio or visual messages, sounds, indicators and the like.

According to aspects of this disclosure, articles of PPE may be configured to transmit the acquired usage data to a personal protective equipment management system (PPEMS), which may be a cloud-based system having an analytics engine configured to process streams of incoming usage data from personal protective equipment deployed and used by a population of workers at various work environments. The analytics engine of the PPEMS may apply the streams of incoming usage data (or at least a subset of the usage data) to one or more models to monitor and predict the likelihood of an occurrence of a safety event for the worker associated with any individual article of PPE. For example, the analytics engine may compare measured parameters (e.g., as measured by the electronic sensors) to known models that characterize activity of a user of an article of PPE, e.g., that represent safe activities, unsafe activities, or activities of concern (which may typically occur prior to unsafe activities) in order to determine the probability of an event occurring.

The analytics engine may generate an output in response to predicting the likelihood of the occurrence of a safety event. For example, the analytics engine may generate an output that indicates a safety event is likely to occur based on data collected from a user of an article of PPE. The output may be used to alert the user of the article of PPE that the safety event is likely to occur, allowing the user to alter their behavior. In other examples, circuitry embedded within the respirators or processors within intermediate data hubs more local to the workers may be programmed via the PPEMS or other mechanism to apply models or rule sets determined by the PPEMS so as to locally generate and output alerts or other preventative measure designed to avoid or mitigate a predicted safety event. In this way, the techniques provide tools to accurately measure and/or monitor operation of a respirator and determine predictive outcomes based on the operation. Although certain examples of this disclosure are provided with respect to certain types of PPE for illustration purposes, the systems, techniques, and devices of this disclosure are applicable to any type of PPE.

FIG. 1 is a block diagram illustrating an example computing system 2 that includes a personal protective equipment management system (PPEMS) 6 for managing personal protective equipment. As described herein, PPEMS allows authorized users to perform preventive occupational health and safety actions and manage inspections and maintenance of safety protective equipment. By interacting with PPEMS 6, safety professionals can, for example, manage area inspections, worker inspections, worker health and safety compliance training.

In general, PPEMS 6 provides data acquisition, monitoring, activity logging, reporting, predictive analytics, PPE control, and alert generation. For example, PPEMS 6 includes an underlying analytics and safety event prediction engine and alerting system in accordance with various examples described herein. In some examples, a safety event may refer to activities of a user of personal protective equipment (PPE), a condition of the PPE, or an environmental condition (e.g., which may be hazardous). In some examples, a safety event may be an injury or worker condition, workplace harm, or regulatory violation. For example, in the context of fall protection equipment, a safety event may be misuse of the fall protection equipment, a user of the fall equipment experiencing a fall, or a failure of the fall protection equipment. In the context of a respirator, a safety event may be misuse of the respirator, a user of the respirator not receiving an appropriate quality and/or quantity of air, or failure of the respirator. A safety event may also be associated with a hazard in the environment in which the PPE is located. In some examples, occurrence of a safety event associated with the article of PPE may include a safety event in the environment in which the PPE is used or a safety event associated with a worker using the article of PPE. In some examples, a safety event may be an indication that PPE, a worker, and/or a worker environment are operating, in use, or acting in a way that is normal operation, where normal operation is a predetermined or predefined condition of acceptable or safe operation, use, or activity. In some examples, a safety event may be an indication of an unsafety condition, wherein the unsafe condition represents a state outside of a set of defined thresholds, rules, or other limits configured by a human operator and/or are machine-generated.

Examples of PPE include, but are not limited to respiratory protection equipment (including disposable respirators, reusable respirators, powered air purifying respirators, and supplied air respirators), protective eyewear, such as visors, goggles, filters or shields (any of which may include augmented reality functionality), protective headwear, such as hard hats, hoods or helmets, hearing protection (including ear plugs and ear muffs), protective shoes, protective gloves, other protective clothing, such as coveralls and aprons, protective articles, such as sensors, safety tools, detectors, global positioning devices, mining cap lamps, fall protection harnesses, exoskeletons, self-retracting lifelines, heating and cooling systems, gas detectors, and any other suitable gear. In some examples, a data hub, such as data hub 14N may be an article of PPE.

As further described below, PPEMS 6 provides an integrated suite of personal safety protection equipment management tools and implements various techniques of this disclosure. That is, PPEMS 6 provides an integrated, end-to-end system for managing personal protective equipment, e.g., safety equipment, used by workers 10 within one or more physical environments 8, which may be construction sites, mining or manufacturing sites or any physical environment. The techniques of this disclosure may be realized within various parts of computing environment 2.

As shown in the example of FIG. 1, system 2 represents a computing environment in which a computing device within of a plurality of physical environments 8A, 8B (collectively, environments 8) electronically communicate with PPEMS 6 via one or more computer networks 4. Each of physical environment 8 represents a physical environment, such as a work environment, in which one or more individuals, such as workers 10, utilize personal protective equipment while engaging in tasks or activities within the respective environment.

In this example, environment 8A is shown as generally as having workers 10, while environment 8B is shown in expanded form to provide a more detailed example. In the example of FIG. 1, a plurality of workers 10A-10N are shown as utilizing respective respirators 13A-13N.

As further described herein, each of respirators 13 includes embedded sensors or monitoring devices and processing electronics configured to capture data in real-time as a user (e.g., worker) engages in activities while wearing the respirator. For example, as described in greater detail herein, respirators 13 may include a number of components (e.g., a head top, a blower, a filter, and the like) respirators 13 may include a number of sensors for sensing or controlling the operation of such components. A head top may include, as examples, a head top visor position sensor, a head top temperature sensor, a head top motion sensor, a head top impact detection sensor, a head top position sensor, a head top battery level sensor, a head top head detection sensor, an ambient noise sensor, or the like. A blower may include, as examples, a blower state sensor, a blower pressure sensor, a blower run time sensor, a blower temperature sensor, a blower battery sensor, a blower motion sensor, a blower impact detection sensor, a blower position sensor, or the like. A filter may include, as examples, a filter presence sensor, a filter type sensor, or the like. Each of the above-noted sensors may generate usage data, as described herein.

In addition, each of respirators 13 may include one or more output devices for outputting data that is indicative of operation of respirators 13 and/or generating and outputting communications to the respective worker 10. For example, respirators 13 may include one or more devices to generate audible feedback (e.g., one or more speakers), visual feedback (e.g., one or more displays, light emitting diodes (LEDs) or the like), or tactile feedback (e.g., a device that vibrates or provides other haptic feedback).

In general, each of environments 8 includes computing facilities (e.g., a local area network) by which respirators 13 are able to communicate with PPEMS 6. For example, environments 8 may be configured with wireless technology, such as 802.11 wireless networks, 802.15 ZigBee networks, and the like. In the example of FIG. 1, environment 8B includes a local network 7 that provides a packet-based transport medium for communicating with PPEMS 6 via network 4. In addition, environment 8B includes a plurality of wireless access points 19A, 19B that may be geographically distributed throughout the environment to provide support for wireless communications throughout the work environment.

Each of respirators 13 is configured to communicate data, such as sensed motions, events and conditions, via wireless communications, such as via 802.11 WiFi protocols, Bluetooth protocol or the like. Respirators 13 may, for example, communicate directly with a wireless access point 19. As another example, each worker 10 may be equipped with a respective one of wearable communication hubs 14A-14M that enable and facilitate communication between respirators 13 and PPEMS 6. For example, respirators 13 as well as other PPEs (such as fall protection equipment, hearing protection, hardhats, or other equipment) for the respective worker 10 may communicate with a respective communication hub 14 via Bluetooth or other short range protocol, and the communication hubs may communicate with PPEMs 6 via wireless communications processed by wireless access points 19. Although shown as wearable devices, hubs 14 may be implemented as stand-alone devices deployed within environment 8B. In some examples, hubs 14 may be articles of PPE. In some examples, communication hubs 14 may be an intrinsically safe computing device, smartphone, wrist- or head-wearable computing device, or any other computing device.

In general, each of hubs 14 operates as a wireless device for respirators 13 relaying communications to and from respirators 13, and may be capable of buffering usage data in case communication is lost with PPEMS 6. Moreover, each of hubs 14 is programmable via PPEMS 6 so that local alert rules may be installed and executed without requiring a connection to the cloud. As such, each of hubs 14 provides a relay of streams of usage data from respirators 13 and/or other PPEs within the respective environment, and provides a local computing environment for localized alerting based on streams of events in the event communication with PPEMS 6 is lost.

As shown in the example of FIG. 1, an environment, such as environment 8B, may also include one or more wireless-enabled beacons, such as beacons 17A-17C, that provide accurate location information within the work environment. For example, beacons 17A-17C may be GPS-enabled such that a controller within the respective beacon may be able to precisely determine the position of the respective beacon. Based on wireless communications with one or more of beacons 17, a given respirator 13 or communication hub 14 worn by a worker 10 is configured to determine the location of the worker within work environment 8B. In this way, event data (e.g., usage data) reported to PPEMS 6 may be stamped with positional information to aid analysis, reporting and analytics performed by the PPEMS.

In addition, an environment, such as environment 8B, may also include one or more wireless-enabled sensing stations, such as sensing stations 21A, 21B. Each sensing station 21 includes one or more sensors and a controller configured to output data indicative of sensed environmental conditions. Moreover, sensing stations 21 may be positioned within respective geographic regions of environment 8B or otherwise interact with beacons 17 to determine respective positions and include such positional information when reporting environmental data to PPEMS 6. As such, PPEMS 6 may be configured to correlate the sensed environmental conditions with the particular regions and, therefore, may utilize the captured environmental data when processing event data received from respirators 13. For example, PPEMS 6 may utilize the environmental data to aid generating alerts or other instructions for respirators 13 and for performing predictive analytics, such as determining any correlations between certain environmental conditions (e.g., heat, humidity, visibility) with abnormal worker behavior or increased safety events. As such, PPEMS 6 may utilize current environmental conditions to aid prediction and avoidance of imminent safety events. Example environmental conditions that may be sensed by sensing stations 21 include but are not limited to temperature, humidity, presence of gas or vapor, pressure, radiation, visibility, wind and the like.

In example implementations, an environment, such as environment 8B, may also include one or more safety stations 15 distributed throughout the environment to provide viewing stations for accessing respirators 13. Safety stations 15 may allow one of workers 10 to check out respirators 13 and/or other safety equipment, verify that safety equipment is appropriate for a particular one of environments 8, and/or exchange data. For example, safety stations 15 may transmit alert rules, software updates, or firmware updates to respirators 13 or other equipment. Safety stations 15 may also receive data cached on respirators 13, hubs 14, and/or other safety equipment. That is, while respirators 13 (and/or data hubs 14) may typically transmit usage data from sensors of respirators 13 to network 4 in real time or near real time, in some instances, respirators 13 (and/or data hubs 14) may not have connectivity to network 4. In such instances, respirators 13 (and/or data hubs 14) may store usage data locally and transmit the usage data to safety stations 15 upon being in proximity with safety stations 15. Safety stations 15 may then upload the data from respirators 13 and connect to network 4. In some examples, a data hub may be an article of PPE.

In addition, each of environments 8 include computing facilities that provide an operating environment for end-user computing devices 16 for interacting with PPEMS 6 via network 4. For example, each of environments 8 typically includes one or more safety managers responsible for overseeing safety compliance within the environment. In general, each user 20 interacts with computing devices 16 to access PPEMS 6. Each of environments 8 may include systems. Similarly, remote users may use computing devices 18 to interact with PPEMS via network 4. For purposes of example, the end-user computing devices 16 may be laptops, desktop computers, mobile devices such as tablets or so-called smart phones and the like.

Users 20, 24 interact with PPEMS 6 to control and actively manage many aspects of safely equipment utilized by workers 10, such as accessing and viewing usage records, analytics and reporting. For example, users 20, 24 may review usage information acquired and stored by PPEMS 6, where the usage information may include data specifying starting and ending times over a time duration (e.g., a day, a week, or the like), data collected during particular events, such as lifts of a visor of respirators 13, removal of respirators 13 from a head of workers 10, changes to operating parameters of respirators 13, status changes to components of respirators 13 (e.g., a low battery event), motion of workers 10, detected impacts to respirators 13 or hubs 14, sensed data acquired from the user, environment data, and the like. In addition, users 20, 24 may interact with PPEMS 6 to perform asset tracking and to schedule maintenance events for individual pieces of safety equipment, e.g., respirators 13, to ensure compliance with any procedures or regulations. PPEMS 6 may allow users 20, 24 to create and complete digital checklists with respect to the maintenance procedures and to synchronize any results of the procedures from computing devices 16, 18 to PPEMS 6.

Further, as described herein, PPEMS 6 integrates an event processing platform configured to process thousand or even millions of concurrent streams of events from digitally enabled PPEs, such as respirators 13. An underlying analytics engine of PPEMS 6 applies historical data and models to the inbound streams to compute assertions, such as identified anomalies or predicted occurrences of safety events based on conditions or behavior patterns of workers 10. Further, PPEMS 6 provides real-time alerting and reporting to notify workers 10 and/or users 20, 24 of any predicted events, anomalies, trends, and the like.

The analytics engine of PPEMS 6 may, in some examples, apply analytics to identify relationships or correlations between sensed worker data, environmental conditions, geographic regions and other factors and analyze the impact on safety events. PPEMS 6 may determine, based on the data acquired across populations of workers 10, which particular activities, possibly within certain geographic region, lead to, or are predicted to lead to, unusually high occurrences of safety events.

In this way, PPEMS 6 tightly integrates comprehensive tools for managing personal protective equipment with an underlying analytics engine and communication system to provide data acquisition, monitoring, activity logging, reporting, behavior analytics and alert generation. Moreover, PPEMS 6 provides a communication system for operation and utilization by and between the various elements of system 2. Users 20, 24 may access PPEMS 6 to view results on any analytics performed by PPEMS 6 on data acquired from workers 10. In some examples, PPEMS 6 may present a web-based interface via a web server (e.g., an HTTP server) or client-side applications may be deployed for devices of computing devices 16, 18 used by users 20, 24, such as desktop computers, laptop computers, mobile devices such as smartphones and tablets, or the like.

In some examples, PPEMS 6 may provide a database query engine for directly querying PPEMS 6 to view acquired safety information, compliance information and any results of the analytic engine, e.g., by the way of dashboards, alert notifications, reports and the like. That is, users 24, 26, or software executing on computing devices 16, 18, may submit queries to PPEMS 6 and receive data corresponding to the queries for graphical output in the form of one or more reports or dashboards. Such dashboards may provide various insights regarding system 2, such as baseline ("normal") operation across worker populations, identifications of any anomalous workers engaging in abnormal activities that may potentially expose the worker to risks, identifications of any geographic regions within environments 2 for which unusually anomalous (e.g., high) safety events have been or are predicted to occur, identifications of any of environments 2 exhibiting anomalous occurrences of safety events relative to other environments, and the like.

As illustrated in detail below, PPEMS 6 may simplify workflows for individuals charged with monitoring and ensure safety compliance for an entity or environment. That is, the techniques of this disclosure may enable active safety management and allow an organization to take preventative or correction actions with respect to certain regions within environments 8, particular pieces of safety equipment or individual workers 10, define and may further allow the entity to implement workflow procedures that are data-driven by an underlying analytical engine.

As one example, the underlying analytical engine of PPEMS 6 may be configured to compute and present customer-defined metrics for worker populations within a given environment 8 or across multiple environments for an organization as a whole. For example, PPEMS 6 may be configured to acquire data and provide aggregated performance metrics and predicted behavior analytics across a worker population (e.g., across workers 10 of either or both of environments 8A, 8B). Furthermore, users 20, 24 may set benchmarks for occurrence of any safety incidences, and PPEMS 6 may track actual performance metrics relative to the benchmarks for individuals or defined worker populations.

As another example, PPEMS 6 may further trigger an alert if certain combinations of conditions are present, e.g., to accelerate examination or service of a safety equipment, such as one of respirators 13. In this manner, PPEMS 6 may identify individual respirators 13 or workers 10 for which the metrics do not meet the benchmarks and prompt the users to intervene and/or perform procedures to improve the metrics relative to the benchmarks, thereby ensuring compliance and actively managing safety for workers 10.

As shown in FIG. 1, environment 8B may include an industrial device 40 and industrial controller device 42. Industrial device 40 may be any physical device that performs an automated operation and is implemented with one or more of electrical, digital, mechanical, optical, and/or chemical technologies, to name only a few example technologies. Industrial device 40 may represent a combination of multiple other industrial devices. Examples of industrial devices may include but are not limited to: conveyors, drives and drive systems, motors, mixers, reactors, robotic devices, control systems, presses, stamps, heating or cooling elements, light sources, drilling devices, etching, devices, printing devices, ventilation devices, and sensing devices, to name only a few examples. Industrial devices may also include combinations of such multiple industrial devices in a factory automation line, station area, or other grouping or assembly of multiple industrial devices.

Industrial device 40 may be controlled by an industrial controller device 42. In some examples, industrial device 40 may be communicatively coupled to industrial controller device 42, such that device 40 and device 42 may communicate between the two devices. For instance, communication link 41 may be a physical or wireless communication channel between industrial controller device 42 and industrial device 40. In some examples, communication link 41 may represent several wired and/or wireless links, and in some examples, other communication devices (e.g., routers, switches, hubs) that communicatively couple together to form a communication channel between devices 40 and 42. In some examples, communication link 41 may represent one or more networks and/or direct connections.

Industrial controller device 42 may be any device that controls, changes, monitors, or otherwise manages industrial device 40. Examples of industrial controller device 42 may include but are not limited to: programmable logic controllers (PLC), I/O (input/output) devices that facilitate communication between other industrial controller devices or sub-components, motor control centers (MCC), drive control devices, manufacturing execution systems (MES), portable computer systems (e.g., desktop and mobile devices), and servers to name only a few examples. Industrial controller device 42 may perform sequential relay control, motion control, process control, distributed control systems, analytics, monitoring, sensing, user interfacing, and networking, to name only a few example operations.

Industrial controller device 42 may generate, send, and/or receive industrial controller data based on the operation of devices 42 and/or 40. Examples of industrial controller data include, but are not limited to: device operating state (normal, abnormal, on, off, locked, unlocked, etc.); temperature; load; weight; rate; component position (e.g., a position of a component of the industrial controller device); timestamp information; user/worker/operator information; properties of materials being processed, measured or otherwise included as part of a process operated by industrial controller device 42.

As shown in FIG. 1, environment 8B may include an environment hazard control device (EHCD) 43. EHCD 43 may receive environmental data from sensing stations 21. Based on one or more safety rules configured at the EHCD 43 and the environment data, EHCD 43 may change the operation of one or more environmental control devices that change one or more conditions of an environment. Environmental control devices may include thermal control devices that alter the air temperature of the environment; ventilation control devices that circulate, exchange, and/or filter air of the environment; noise control devices that dampen or otherwise alter the sound intensity within an environment; and/or radiation control devices that shield or otherwise impede radiation within an environment.

As described in this disclosure, data may be generated by sensing stations, personal protective equipment (including data hubs), smartphones and desktop computers, safety stations, industrial devices, environmental hazard control devices, and industrial controller devices. In some examples, different sets of data may be combined, analyzed, or processed together by a computing device through operations, which may be referred to as data fusion, in which multiple data sources are integrated to produce more consistent, accurate, timely, and/or useful information than that provided by any individual data source. Various techniques may be applied in data fusion, such as identifying correlations, clusters, anomalies; determining that one or more rules have been satisfied; and/or determining one or more probabilities or likelihoods based on one or more models. Techniques of this disclosure may perform data fusion on data generated by one or more of sensing stations, personal protective equipment (including data hubs), smartphones and desktop computers, safety stations, industrial devices, environmental hazard control devices, and industrial controller devices to determine, detect, and/or identify safety events. In some examples, a safety event may refer to operation or state of an industrial controller device or industrial device that does not satisfy one or more rules, limits, or thresholds. In some examples, a normal operation or state of an industrial controller device or industrial device may satisfy or be within one or more rules, limits, or thresholds. In some examples an abnormal operation or state of an industrial controller device or industrial device may not satisfy or may not be within one or more rules, limits, or thresholds. In some examples, the rules, limits, or thresholds or may configured by a person at a computing device. In other examples, the rules, limits, or thresholds may be machine generated using one or more learning techniques for models that are described in this disclosure.

Techniques of this disclosure may be implemented in a data fusion component (DFC), such as illustrated by DFCs 44A-44G ("DFCs 44"). DFCs 44 may be implemented in hardware, software, or a combination of hardware and software. DFCs 44 may be implemented in various ways. For example, DFCs 44 may be implemented as downloadable or pre-installed applications or "apps." In another example, DFCs 44 may be implemented as part of a hardware unit of one or more computing devices. In another example, DFCs 44 may be implemented as part of an operating system of computing device 2. In some examples, functionality of a DFC may be distributed across multiple devices, wherein such devices communicate with one another to perform the functionality of the DFC. DFCs 44 may be included in multiple devices as shown in FIG. 1, although DFCs 44 may be included in other devices or components not shown. For instance, a manufacturing execution system may operate or otherwise execute on computing device, and the manufacturing execution system may also include a DFC. Similarly, a computing device, such as computing devices 18 of remote users may include DFCs.

In accordance with techniques of this disclosure, system 2 may include an article of personal protective equipment (PPE) 13N that includes a communication component. System 2 may also include an industrial controller device 42 that is configured to control an industrial device 40 and includes a communication component. One or more computing devices may be communicatively coupled to the article of PPE and the industrial controller device, such as data hub 14N, safety station 15, computing devices 16, PPEMS 6, and one or more of the computing devices may include DFCs. Although various of the following examples are described with respect to DFC 44F and/or DFC 44B, any device that includes a DFC may perform the techniques described with the respect to DFC 44F and/or DFC 44B.

In the example of FIG. 1, DFC 44F and/or DFC 44B may receive PPE data from article of PPE 44E via data hub 14N. DFC 44F and/or DFC 44B may receive industrial controller data from the industrial controller device 44F. DFC 44F and/or DFC 44B may determine, based at least in part on a set of the PPE data that temporally corresponds to a set of the industrial controller data, an occurrence of a safety event. In some PPE data that temporally corresponds to industrial controller data may be PPE data that corresponds to a timestamp or time period that corresponds to the industrial controller data. For instance, the industrial controller data and PPE data may have matching or overlapping timestamps that indicate when the respective data was created. In some examples, the industrial controller data and PPE data may have timestamps that indicate when the respective data was created, where the respective timestamps for the industrial controller data and PPE data were generated within a threshold time period of one another. In some examples, PPE data that temporally corresponds to industrial controller data may be PPE data that is contemporaneously generated with the industrial controller data. DFC 44F and/or DFC 44B may perform, based at least in part on the determination of the safety event, at least one operation.

In some examples, DFC 44F and/or DFC 44B may select, from the set of PPE data, at least one PPE identifier that corresponds to the article of PPE. DFC 44F and/or DFC 44B may select, based at least in part on an industrial controller identifier of the set of industrial controller data that corresponds to industrial controller device 42, an inspection history of industrial controller device 42. In some examples, an inspection history may include data that indicates one or more of a person who inspected a device, a timestamp when the inspection occurred, and/or the result of the inspection. DFC 44F and/or DFC 44B may determine a safety event based at least in part on a determination that the inspection history of the industrial controller device does not satisfy at least one of a threshold or a rule that is configured for the industrial controller device. In some examples, the threshold or rule may be user configured or machine generated. Thresholds or rules as described throughout this disclosure may be based on one or more safety regulations, laws, or other policies. In some examples, the threshold or the safety rule is based at least in part on one of a particular timestamp or a period of time.

In some examples, DFC 44F and/or DFC 44B may determine an identifier of a worker that corresponds to the article of PPE. DFC 44F and/or DFC 44B may select, based at least in part on the identifier of a worker, a training history that indicates training completed by the worker. In some examples, the training history may include data that indicates a training identifier, a description of the training, a timestamp when the training was due, a timestamp when the training was completed, and/or an identifier of the worker who performed the training to name only a few examples. DFC 44F and/or DFC 44B may select, based at least in part on an industrial controller identifier of the set of industrial controller data that corresponds to the industrial controller device, a training rule that is configured for the industrial controller device. A training rule may be data that specifies a condition that must be satisfied with respect to device. For instance, the training rule may specify that particular training must be completed by a worker in order to be authorized to operate an industrial device or other device. DFC 44F and/or DFC 44B may determine the safety event based at least in on a determination by the computing device that the training history completed by the worker does not satisfy the training rule configured for the industrial controller device.

In some examples, a particular worker may not have training that satisfies the training rule, but another worker may have training that satisfies the training rule. DFC 44F and/or DFC 44B may identify the other worker associated with the sufficient training history that satisfies the training rule configured for the instruction controller device. DFC 44F and/or DFC 44B may generate for output a recommendation that the second worker operate the industrial device. The recommendation may include information such as, but not limited to, an instruction to a worker to operate or not operate an industrial device, a location of the industrial device, a route to the industrial device, or an indication of training that must be completed to operate the industrial device.

In some examples, DFC 44F and/or DFC 44B may determine an identifier of a worker associated with the article of PPE. DFC 44F and/or DFC 44B may select, based at least in part on the identifier of the worker, at least one authorization element that indicates whether the worker is authorized to operate the industrial device. In some examples, an authorization element may be information such as a credential, token, flag, or other data that indicates an authorization for operating and industrial device. DFC 44F and/or DFC 44B may select, based at least in part on an industrial controller identifier of the set of industrial controller data that corresponds to the industrial controller device, an authorization rule configured for the industrial controller device. An authorization rule may be data that specifies a condition that must be satisfied for authorization to occur. For instance, an authorization rule may determine whether an authorization element is sufficient to operate the industrial device. The rule may be human-configured or machine-generated. DFC 44F and/or DFC 44B may determine a safety event based at least in on a determination by the computing device that the authorization element for the worker does not satisfy the authorization rule configured for the industrial controller device.

In some examples, a particular worker may not have a sufficient authorization element to satisfy the authorization rule, but another worker may have such sufficient authorization element. DFC 44F and/or DFC 44B may identify the other worker associated with a sufficient authorization element that satisfies the authorization rule configured for the industrial controller device. DFC 44F and/or DFC 44B may generate for output a recommendation that the second worker operate the industrial device. The recommendation may include information such as, but not limited to, an instruction to a worker to operate or not operate an industrial device, a location of the industrial device, a route to the industrial device, or an indication of training that must be completed to operate the industrial device.

In some examples, DFC 44F and/or DFC 44B may select, from a set of PPE data, at least one PPE identifier that corresponds to the article of PPE. DFC 44F and/or DFC 44B may determine, from the set of industrial controller data and based at least in part on an industrial controller identifier that corresponds to the industrial controller device, a work zone that includes the industrial device. The work zone may comprise a region encompassed by a defined boundary. In some examples, the defined boundary may be represented in data with coordinates, perimeters, or other indicia of the boundary. DFC 44F and/or DFC 44B may determine the safety event based at least in part on a determination by the computing device that the article of PPE does not satisfy an access rule configured to restrict entry into the work zone that includes the industrial controller device or environmental hazard control device 43. In some examples, the access rule may specify a condition that must be satisfied to enter a work zone. The access rule may be human-configured or machine generated.

In some examples, DFC 44F and/or DFC 44B may select, based at least in part on an industrial controller identifier of the set of industrial controller data that corresponds to industrial controller device 42, operating data of the industrial controller device 42 that indicates one or more operating metrics for the industrial device 40 and/or industrial controller device 42. The one or more operating metrics may indicate data about operation of industrial device 40, industrial controller device 42, or environmental hazard control device 43. DFC 44F and/or DFC 44B may determine the safety event based at least in part on an identifier associated with a worker and a determination DFC 44F and/or DFC 44B that at least one operating metric for the industrial device does not satisfy an operating rule configured for the industrial device. In some examples, the operating rule may indicate a condition or threshold that must be satisfied for the industrial device 40, industrial controller device 42, or environmental hazard control device 43. Operating metrics may include but are not limited to: temperature, output rate, vibration, sound emission, component speed, remaining component life, operating rate, air or sound hazard level, radiation level, or any other metric that indicates a characteristic of the operation of industrial device 40 and/or industrial controller device 42, and/or environmental hazard control device 43.

In some examples, DFC 44F and/or DFC 44B may select, from the set of PPE data, first positional context data that indicates at least one physical position of a first worker associated with the article of PPE. In some examples, DFC 44F and/or DFC 44B may determine a safety event based at least in part on the first positional context data and second positional context data associated with at least one of a second worker in proximity to the first worker or the industrial device in proximity to the first worker. In some examples, the first positional context data comprises at least one of orientation data that indicates an orientation of the first worker or location data that indicates a location of the first worker.

In some examples, DFC 44D may detect an input that initiates a broadcast of diagnostic self-check messages. May DFC 44D identify, in response to the input, at least article of PPE 13N. DFC 44D may broadcast, based on identifying article of PPE 13N, a diagnostic self-check message to the article of PPE, wherein the article of PPE receives the self-check message at a communication component of the article of PPE. DFC 44D, in response to receiving a diagnostic acknowledgement message from the article of PPE that has performed a diagnostic self-check, may determine whether the set of diagnostic acknowledgement messages satisfy one or more self-check criteria based at least in part on the set of the industrial controller data. DFC 44D may determine a safety event based at least in part on whether the one or more self-check criteria are satisfied.

In some examples, to perform, based at least in part on the determination of the safety event, the at least one operation, DFC 44F and/or DFC 44B may, in response to determining the safety event, generate for output at least one of an audible indication, a visual indication, or a tactile indication. In some examples, the at least one of the visual or audible indication includes a message that indicates that operation of industrial device 40 will stop after a threshold period of time. In some examples, to perform, based at least in part on the determination of the safety event, the at least one operation, DFC 44F and/or DFC 44B may send the output to at least one of the article of PPE, the industrial controller device 42, or a remote computing device. In some examples, to perform, based at least in part on the determination of the safety event, the at least one operation, DFC 44F and/or DFC 44B may, in response to determining the safety event, generate for output a message that changes an operation of the industrial controller device 42 or the industrial device 40 or EHCS 43. In some examples, the message that changes the operation of the industrial controller device comprises information that stops the operation of the industrial device. In some examples, the message that changes the operation of the industrial device comprises information that changes a position of a component of the industrial device.

In some examples, DFC 44F and/or DFC 44B may select a set of stored process operations that define a set of process operations to be performed by a worker with respect to the industrial device. DFC 44F and/or DFC 44B may determine, based at least in part on one or more of the set of PPE data and a set of the industrial controller data, that the worker has failed to perform at least one process operation in the set of process operations. DFC 44F and/or DFC 44B may determine the safety event based at least in part on the determination that the worker has failed to perform the at least one process operation in the set of process operations.

In some examples, DFC 44F and/or DFC 44B may select acoustic data from the industrial controller data, wherein the acoustic data indicates at least one of an amount or intensity of sound emitted by the industrial device. DFC 44F and/or DFC 44B may determine that the amount or intensity of the sound satisfies a threshold. DFC 44F and/or DFC 44B may determine the safety event based at least in part on determining that the amount or intensity of the sound satisfies the threshold.

In some examples, DFC 44F and/or DFC 44B may select worker data comprising a plurality of identifiers that identify a respective plurality of workers. DFC 44F and/or DFC 44B may determine a respective proximity of each respective worker to the industrial device. DFC 44F and/or DFC 44B may determine that the respective proximities collectively satisfy a proximity threshold. DFC 44F and/or DFC 44B may determine the safety event based at least in part on determining that the respective proximities collectively satisfy a proximity threshold. In some examples, the proximity threshold may be user configured or machine determine. The proximity threshold may be based on one or more safety rules, policies, or laws. The proximity threshold may specific a minimum distance that a worker or set of workers must be separated from the industrial device or industrial controller device.

In some examples, after the occurrence of an emergency event, one or more location beacons may be positioned near the emergency event. DFC 44F and/or DFC 44B may configure an identifier of a location beacon in association with information that describes the emergency event. The location beacon may be positioned within a threshold distance of a location of the emergency event. DFC 44F and/or DFC 44B may send at least one rule to at least one of the article of PPE or the industrial controller device. The at least one rule may be based at least in part on the emergency event. Example rules may specify an exit route, PPE requirements for the emergency event, operations to be performed at the industrial controller device or industrial device, alerts/notifications, or any other data related to the emergency event.

In some examples, DFC 44F and/or DFC 44B may select worker fatigue data from a set of PPE data. DFC 44F and/or DFC 44B may determine the safety event based at least in part on the industrial controller data and the worker fatigue data. In some examples, the worker fatigue data comprises at least one of physiological data that indicates a physiological characteristic of the worker, motion data that indicates motion of the worker, or worker image data that is based at least in part on imaging of the worker.

In some examples, DFC 44F and/or DFC 44B may select PPE fit data from a set of PPE data. The PPE fit data may indicate a fit characteristic of the article of PPE relative to a worker associated with the article of PPE. DFC 44F and/or DFC 44B may determine the safety event based at least in part on the industrial controller data and the PPE fit data. In some examples, the PPE fit data indicates at least one of a fit of a hearing protection device relative to the worker, a fit of a fall protection device relative to the worker, or a fit of a respiratory protection device relative to the worker.

In some examples, DFC 44F and/or DFC 44B may select worker productivity data from the set of PPE data. The worker productivity data indicates a productivity characteristic of a worker relative to industrial device 42. DFC 44F and/or DFC 44B may determine the safety event based at least in part on the industrial controller data and the worker productivity data. The worker productivity data may include, but is not limited to at least one of worker break data that indicates a duration or quantity of worker breaks or a rate at which a worker is operating the industrial device. In some examples, DFC 44F and/or DFC 44B may generate for display, a graphical user interface that contemporaneously includes at least a first graphical element based at least in part on the set of PPE data and a second graphical element based at least in part on the set of industrial controller data.

In some examples, a work environment may include a set of safety requirements that are configured for DFC 44F and/or DFC 44B. The safety requirements may specify actions that a worker must take for the work environment. DFC 44F and/or DFC 44B may receive streams of data that indicate actions taken by the worker with respect to PPE, the worker environment (including hazards), the industrial device, and the industrial controller device. DFC 44F and/or DFC 44B may measure deviations in the streams of data from baseline or expected values for the safety requirements. If the deviations satisfy a threshold, DFC 44F and/or DFC 44B may determine a safety event. In some examples, DFC 44F and/or DFC 44B may be configured with a hierarchy of thresholds, such that a first threshold may generate a warning or alert that a deviation has occurred, but a second threshold may disable the industrial controller and/or industrial device. A third threshold may require that the worker exit the work environment. A fourth threshold may require that maintenance be performed on PPE, industrial controller device, and/or industrial device. Any number of thresholds may be configured at DFC 44F and/or DFC 44B with any number of corresponding outputs (e.g., recommendations, alerts, access controls, device operation changes, etc.).

In some examples, data may be communicated between any one or more of the computing devices using a mesh network, in which the infrastructure nodes (two or more devices of FIG. 1) connect directly, dynamically and non-hierarchically to any number of other nodes and cooperate with one another to efficiently route data from/to clients. For instance, data generated by industrial controller device 42 may be transmitted to DFC 44B via data hub 14N, which transmits the data to wireless access points 19A, and wherein wireless access points 19A transmits the data via network 4 to PPEMS6, which includes DFC 44B. Any number of other devices and routes existing between such devices of FIG. 1 may be used to communicate data between the respective devices using a mesh network.

In some examples, worker 10N may provide voice commands to any number of devices in FIG. 1. For instance, worker 10N may provide voice commands to industrial controller device 42, data hub 14N, PPE 13N or any other device that includes a voice command component. A voice command component may perform natural language processing or other recognition techniques on audible sounds received from worker 10N. Based on the processing of the audible sounds, the voice command component may perform one or more operations. For instance, the voice command component may send a message to one or more devices, change the operation of one or more device, or send the audible sounds to one or more other devices, to name only a few example operations that may be performed by the voice command component in response to receiving the audible sources.

In some examples, one or more image capture devices may be included within environment 8. For instance, an image capture device may capture still and/or moving images (e.g. video). Image capture devices may be stationary or movable. In some examples, the image capture device may be integrated in an article of PPE, industrial controller device, industrial device, or mounted/positioned in a stationary manner from a floor, wall, ceiling, or other supporting surface of environment 8 or objects within environment 8. Image data, such as still images and video, generated by image capture devices may be used to perform the techniques of this disclosure. For instance, objects may be recognized within the image data and used in conjunction with PPE data, industrial controller data, and/or environmental hazard data to determine safety events. As an example, a computing device may detect a particular object, a position of an object, or state of an object within image data, and when processed with PPE data, industrial controller data, and/or environmental data, may be used to determine a safety event.

In some examples, one or more audio capture devices may be included within environment 8. For instance, an audio capture device may capture sound or audio information. Audio capture devices may be stationary or movable. In some examples, the audio capture device may be integrated in an article of PPE, industrial controller device, industrial device, or mounted/positioned in a stationary manner from a floor, wall, ceiling, or other supporting surface of environment 8 or objects within environment 8. Audio data that represents an audio signal or other sound generated by audio capture devices may be used to perform the techniques of this disclosure. For instance, audio signatures may be recognized within the audio data and used in conjunction with PPE data, industrial controller data, and/or environmental hazard data to determine safety events. As an example, a computing device may detect a particular audio signature, and when processed with PPE data, industrial controller data, and/or environmental data, may be used to determine a safety event.

In some examples, DFC 44F and/or DFC 44B receive data from EHCD 43 that indicates environmental data and/or changes in operation to one or more environmental control devices. Based on the environmental data and/or changes in operation to one or more environmental control devices, in conjunction with one or more of PPE data and/or industrial controller device data, DFC 44F and/or DFC 44B may determine a safety event. For instance, EHCD 43 may be configured with one or more safety rules that are human-defined and/or machine-configured. The safety rules may be defined based on safety regulations, laws or other policies. In some examples, a ventilation control device may be configured to provide an air turnover rate that maintains airborne contaminants below a threshold. Data from EHCD 43 that is received by DFC 44F and/or DFC 44B may indicate that the air turnover rate has fallen below the threshold and/or does not satisfy the threshold. The cause of the deceased air turnover rate may be the result of disrepair, missed inspection, wear, or abnormal contaminant concentrations above a particular level. PPE may further have an assigned protection factor that defines a maximum use concentration that will protect the worker. The maximum use concentration may be a legally allowed limit of contaminant exposure permitted for the PPE. In the current example, DFC 44F and/or DFC 44B may determine that air turnover rate has fallen below the threshold required to maintain compliance with the maximum use concentration for the article of PPE, and, accordingly, DFC 44F and/or DFC 44B may determine a safety event.

As another example, DFC 44F and/or DFC 44B may determine that a sound exposure levels and/or sound amounts processed by EHCD 43 for a sound control device in environment 8B exceed a threshold. DFC 44F and/or DFC 44B may determine that, based on the type of hearing PPE, the worker has exceeded his or her sound exposure for a defined period of time, and, accordingly, DFC 44F and/or DFC 44B may determine a safety event. Although respiratory and sound hazards have been described for illustration purposes with respect to EHCD 43, the techniques may be used for any type of hazard and/or PPE.

In some examples, DFC 44F and/or DFC 44B may receive data that indicates worker distress or impairment. Examples of such data may include motion data, physiological data, visual data, or any other suitable data to determine that a worker is distressed or impaired. In combination with environmental data and/or industrial controller data, DFC 44F and/or DFC 44B may determine a safety event. For instance, data indicating an impaired worker, operating at an industrial device that is turned on, may cause DFC 44F and/or DFC 44B to generate an alert, disable the industrial device or perform one or more operations, such as those described in this disclosure with respect to determining a safety event.

Figure 2:
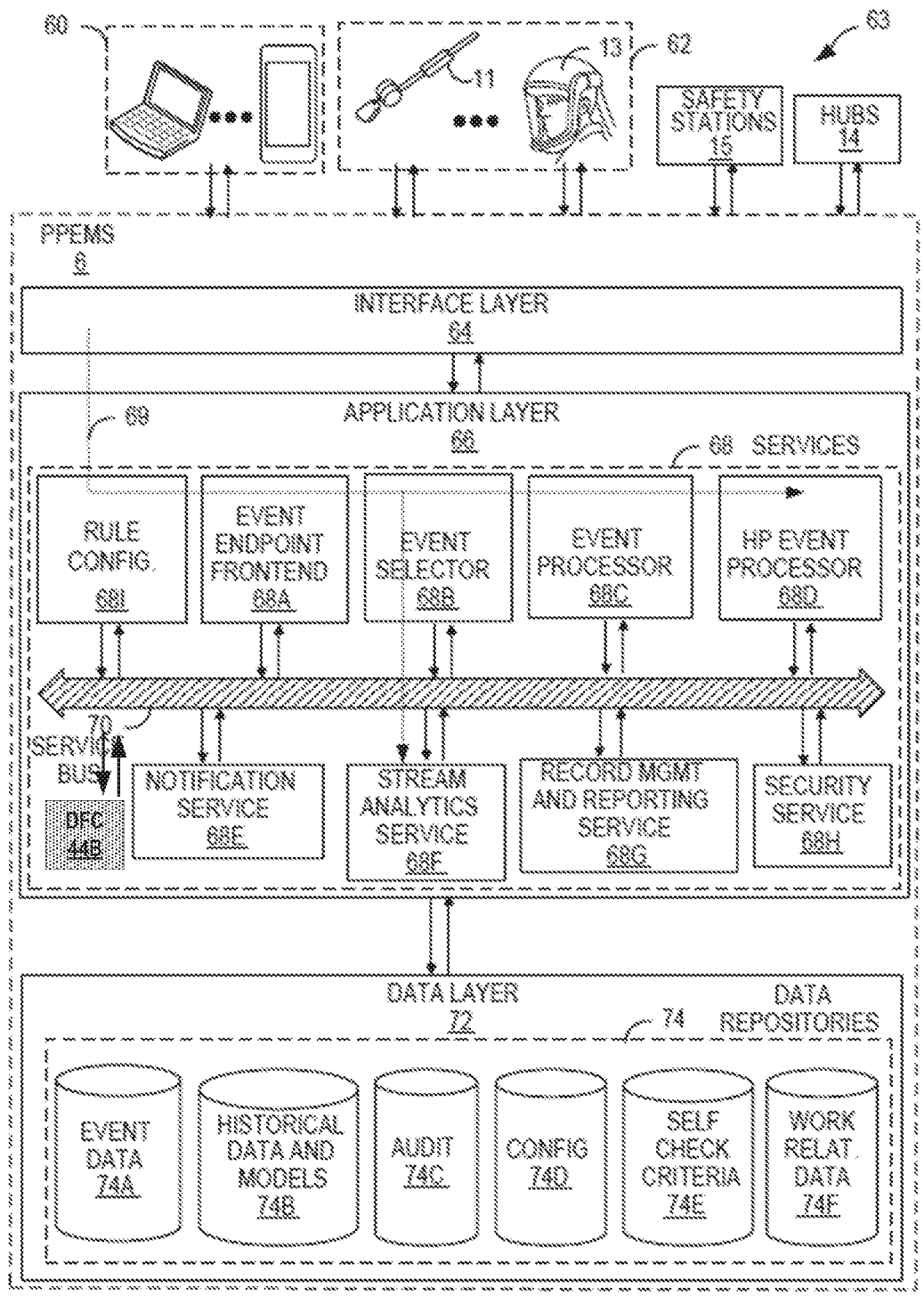
FIG. 2 is a block diagram illustrating an operating perspective of the personal protective equipment management system shown in FIG. 1 in accordance with various techniques of this disclosure.

FIG. 2 is a block diagram providing an operating perspective of PPEMS 6 when hosted as cloud-based platform capable of supporting multiple, distinct work environments 8 having an overall population of workers 10 that have a variety of communication enabled personal protective equipment (PPE), such as safety release lines (SRLs) 11, respirators 13, safety helmets, hearing protection or other safety equipment. In the example of FIG. 2, the components of PPEMS 6 are arranged according to multiple logical layers that implement the techniques of the disclosure. Each layer may be implemented by one or more modules comprised of hardware, software, or a combination of hardware and software.

In FIG. 2, personal protective equipment (PPEs) 62, such as SRLs 11, respirators 13 and/or other equipment, either directly or by way of hubs 14, as well as computing devices 60, operate as clients 63 that communicate with PPEMS 6 via interface layer 64. Computing devices 60 typically execute client software applications, such as desktop applications, mobile applications, and web applications. Computing devices 60 may represent any of computing devices 16, 18 of FIG. 1. Examples of computing devices 60 may include, but are not limited to a portable or mobile computing device (e.g., smartphone, wearable computing device, tablet), laptop computers, desktop computers, smart television platforms, and servers, to name only a few examples.

As further described in this disclosure, PPEs 62 communicate with PPEMS 6 (directly or via hubs 14) to provide streams of data acquired from embedded sensors and other monitoring circuitry and receive from PPEMS 6 alerts, configuration and other communications. Client applications executing on computing devices 60 may communicate with PPEMS 6 to send and receive information that is retrieved, stored, generated, and/or otherwise processed by services 68. For instance, the client applications may request and edit safety event information including analytical data stored at and/or managed by PPEMS 6. In some examples, client applications 61 may request and display aggregate safety event information that summarizes or otherwise aggregates numerous individual instances of safety events and corresponding data acquired from PPEs 62 and or generated by PPEMS 6. The client applications may interact with PPEMS 6 to query for analytics information about past and predicted safety events, behavior trends of workers 10, to name only a few examples. In some examples, the client applications may output for display information received from PPEMS 6 to visualize such information for users of clients 63. As further illustrated and described in below, PPEMS 6 may provide information to the client applications, which the client applications output for display in user interfaces.

Clients applications executing on computing devices 60 may be implemented for different platforms but include similar or the same functionality. For instance, a client application may be a desktop application compiled to run on a desktop operating system, such as Microsoft Windows, Apple OS X, or Linux, to name only a few examples. As another example, a client application may be a mobile application compiled to run on a mobile operating system, such as Google Android, Apple iOS, Microsoft Windows Mobile, or BlackBerry OS to name only a few examples. As another example, a client application may be a web application such as a web browser that displays web pages received from PPEMS 6. In the example of a web application, PPEMS 6 may receive requests from the web application (e.g., the web browser), process the requests, and send one or more responses back to the web application. In this way, the collection of web pages, the client-side processing web application, and the server-side processing performed by PPEMS 6 collectively provides the functionality to perform techniques of this disclosure. In this way, client applications use various services of PPEMS 6 in accordance with techniques of this disclosure, and the applications may operate within various different computing environment (e.g., embedded circuitry or processor of a PPE, a desktop operating system, mobile operating system, or web browser, to name only a few examples).

As shown in FIG. 2, PPEMS 6 includes an interface layer 64 that represents a set of application programming interfaces (API) or protocol interface presented and supported by PPEMS 6. Interface layer 64 initially receives messages from any of clients 63 for further processing at PPEMS 6. Interface layer 64 may therefore provide one or more interfaces that are available to client applications executing on clients 63. In some examples, the interfaces may be application programming interfaces (APIs) that are accessible over a network. Interface layer 64 may be implemented with one or more web servers. The one or more web servers may receive incoming requests, process and/or forward information from the requests to services 68, and provide one or more responses, based on information received from services 68, to the client application that initially sent the request. In some examples, the one or more web servers that implement interface layer 64 may include a runtime environment to deploy program logic that provides the one or more interfaces. As further described below, each service may provide a group of one or more interfaces that are accessible via interface layer 64.

In some examples, interface layer 64 may provide Representational State Transfer (RESTful) interfaces that use HTTP methods to interact with services and manipulate resources of PPEMS 6. In such examples, services 68 may generate JavaScript Object Notation (JSON) messages that interface layer 64 sends back to the client application 61 that submitted the initial request. In some examples, interface layer 64 provides web services using Simple Object Access Protocol (SOAP) to process requests from client applications 61. In still other examples, interface layer 64 may use Remote Procedure Calls (RPC) to process requests from clients 63. Upon receiving a request from a client application to use one or more services 68, interface layer 64 sends the information to application layer 66, which includes services 68.

As shown in FIG. 2, PPEMS 6 also includes an application layer 66 that represents a collection of services for implementing much of the underlying operations of PPEMS 6. Application layer 66 receives information included in requests received from client applications 61 and further processes the information according to one or more of services 68 invoked by the requests. Application layer 66 may be implemented as one or more discrete software services executing on one or more application servers, e.g., physical or virtual machines. That is, the application servers provide runtime environments for execution of services 68. In some examples, the functionality interface layer 64 as described above and the functionality of application layer 66 may be implemented at the same server.

Application layer 66 may include one or more separate software services 68, e.g., processes that communicate, e.g., via a logical service bus 70 as one example. Service bus 70 generally represents a logical interconnections or set of interfaces that allows different services to send messages to other services, such as by a publish/subscription communication model. For instance, each of services 68 may subscribe to specific types of messages based on criteria set for the respective service. When a service publishes a message of a particular type on service bus 70, other services that subscribe to messages of that type will receive the message. In this way, each of services 68 may communicate information to one another. As another example, services 68 may communicate in point-to-point fashion using sockets or other communication mechanism. Before describing the functionality of each of services 68, the layers are briefly described herein.

Data layer 72 of PPEMS 6 represents a data repository that provides persistence for information in PPEMS 6 using one or more data repositories 74. A data repository, generally, may be any data structure or software that stores and/or manages data. Examples of data repositories include but are not limited to relational databases, multi-dimensional databases, maps, and hash tables, to name only a few examples. Data layer 72 may be implemented using Relational Database Management System (RDBMS) software to manage information in data repositories 74. The RDBMS software may manage one or more data repositories 74, which may be accessed using Structured Query Language (SQL). Information in the one or more databases may be stored, retrieved, and modified using the RDBMS software. In some examples, data layer 72 may be implemented using an Object Database Management System (ODBMS), Online Analytical Processing (OLAP) database or other suitable data management system.

As shown in FIG. 2, each of services 68A-68I ("services 68") is implemented in a modular form within PPEMS 6. Although shown as separate modules for each service, in some examples the functionality of two or more services may be combined into a single module or component. Each of services 68 may be implemented in software, hardware, or a combination of hardware and software. Moreover, services 68 may be implemented as standalone devices, separate virtual machines or containers, processes, threads or software instructions generally for execution on one or more physical processors.

In some examples, one or more of services 68 may each provide one or more interfaces that are exposed through interface layer 64. Accordingly, client applications of computing devices 60 may call one or more interfaces of one or more of services 68 to perform techniques of this disclosure.

In accordance with techniques of the disclosure, services 68 may include an event processing platform including an event endpoint frontend 68A, event selector 68B, event processor 68C and high priority (HP) event processor 68D. Event endpoint frontend 68A operates as a front end interface for receiving and sending communications to PPEs 62 and hubs 14. In other words, event endpoint frontend 68A operates to as a front line interface to safety equipment deployed within environments 8 and utilized by workers 10. In some instances, event endpoint frontend 68A may be implemented as a plurality of tasks or jobs spawned to receive individual inbound communications of event streams 69 from the PPEs 62 carrying data sensed and captured by the safety equipment. When receiving event streams 69, for example, event endpoint frontend 68A may spawn tasks to quickly enqueue an inbound communication, referred to as an event, and close the communication session, thereby providing high-speed processing and scalability. Each incoming communication may, for example, carry data recently captured data representing sensed conditions, motions, temperatures, actions or other data, generally referred to as events. Communications exchanged between the event endpoint frontend 68A and the PPEs may be real-time or pseudo real-time depending on communication delays and continuity.

Event selector 68B operates on the stream of events 69 received from PPEs 62 and/or hubs 14 via frontend 68A and determines, based on rules or classifications, priorities associated with the incoming events. Based on the priorities, event selector 68B enqueues the events for subsequent processing by event processor 68C or high priority (HP) event processor 68D. Additional computational resources and objects may be dedicated to HP event processor 68D so as to ensure responsiveness to critical events, such as incorrect usage of PPEs, use of incorrect filters and/or respirators based on geographic locations and conditions, failure to properly secure SRLs 11 and the like. Responsive to processing high priority events, HP event processor 68D may immediately invoke notification service 68E to generate alerts, instructions, warnings or other similar messages to be output to SRLs 11, respirators 13, hubs 14 and/or remote users 20, 24. Events not classified as high priority are consumed and processed by event processor 68C.

In general, event processor 68C or high priority (HP) event processor 68D operate on the incoming streams of events to update event data 74A within data repositories 74. In general, event data 74A may include all or a subset of usage data obtained from PPEs 62. For example, in some instances, event data 74A may include entire streams of samples of data obtained from electronic sensors of PPEs 62. In other instances, event data 74A may include a subset of such data, e.g., associated with a particular time period or activity of PPEs 62.

Event processors 68C, 68D may create, read, update, and delete event information stored in event data 74A. Event information for may be stored in a respective database record as a structure that includes name/value pairs of information, such as data tables specified in row/column format. For instance, a name (e.g., column) may be "worker ID" and a value may be an employee identification number. An event record may include information such as, but not limited to: worker identification, PPE identification, acquisition timestamp(s) and data indicative of one or more sensed parameters.

In addition, event selector 68B directs the incoming stream of events to stream analytics service 68F, which is configured to perform in depth processing of the incoming stream of events to perform real-time analytics. Stream analytics service 68F may, for example, be configured to process and compare multiple streams of event data 74A with historical data and models 74B in real-time as event data 74A is received. In this way, stream analytic service 68D may be configured to detect anomalies, transform incoming event data values, trigger alerts upon detecting safety concerns based on conditions or worker behaviors. Historical data and models 74B may include, for example, specified safety rules, business rules and the like. In addition, stream analytic service 68D may generate output for communicating to PPPEs 62 by notification service 68F or computing devices 60 by way of record management and reporting service 68D.

In this way, analytics service 68F processes inbound streams of events, potentially hundreds or thousands of streams of events, from enabled safety PPEs 62 utilized by workers 10 within environments 8 to apply historical data and models 74B to compute assertions, such as identified anomalies or predicted occurrences of imminent safety events based on conditions or behavior patterns of the workers. Analytics service may 68D publish the assertions to notification service 68F and/or record management by service bus 70 for output to any of clients 63.

In this way, analytics service 68F may be configured as an active safety management system that predicts imminent safety concerns and provides real-time alerting and reporting. In addition, analytics service 68F may be a decision support system that provides techniques for processing inbound streams of event data to generate assertions in the form of statistics, conclusions, and/or recommendations on an aggregate or individualized worker and/or PPE basis for enterprises, safety officers and other remote users. For instance, analytics service 68F may apply historical data and models 74B to determine, for a particular worker, the likelihood that a safety event is imminent for the worker based on detected behavior or activity patterns, environmental conditions and geographic locations. In some examples, analytics service 68F may determine whether a worker is currently impaired, e.g., due to exhaustion, sickness or alcohol/drug use, and may require intervention to prevent safety events. As yet another example, analytics service 68F may provide comparative ratings of workers or type of safety equipment in a particular environment 8.

Hence, analytics service 68F may maintain or otherwise use one or more models that provide risk metrics to predict safety events. Analytics service 68F may also generate order sets, recommendations, and quality measures. In some examples, analytics service 68F may generate user interfaces based on processing information stored by PPEMS 6 to provide actionable information to any of clients 63. For example, analytics service 68F may generate dashboards, alert notifications, reports and the like for output at any of clients 63. Such information may provide various insights regarding baseline ("normal") operation across worker populations, identifications of any anomalous workers engaging in abnormal activities that may potentially expose the worker to risks, identifications of any geographic regions within environments for which unusually anomalous (e.g., high) safety events have been or are predicted to occur, identifications of any of environments exhibiting anomalous occurrences of safety events relative to other environments, and the like.

Although other technologies can be used, in one example implementation, analytics service 68F utilizes machine learning when operating on streams of safety events so as to perform real-time analytics. That is, analytics service 68F includes executable code generated by application of machine learning to training data of event streams and known safety events to detect patterns. The executable code may take the form of software instructions or rule sets and is generally referred to as a model that can subsequently be applied to event streams 69 for detecting similar patterns and predicting upcoming events.

Analytics service 68F may, in some example, generate separate models for a particular worker, a particular population of workers, a particular environment, or combinations thereof. Analytics service 68F may update the models based on usage data received from PPEs 62. For example, analytics service 68F may update the models for a particular worker, a particular population of workers, a particular environment, or combinations thereof based on data received from PPEs 62. In some examples, usage data may include incident reports, air monitoring systems, manufacturing production systems, or any other information that may be used to a train a model.

Alternatively, or in addition, analytics service 68F may communicate all or portions of the generated code and/or the machine learning models to hubs 16 (or PPEs 62) for execution thereon so as to provide local alerting in near-real time to PPEs. Example machine learning techniques that may be employed to generate models 74B can include various learning styles, such as supervised learning, unsupervised learning, and semi-supervised learning. Example types of algorithms include Bayesian algorithms, Clustering algorithms, decision-tree algorithms, regularization algorithms, regression algorithms, instance-based algorithms, artificial neural network algorithms, deep learning algorithms, dimensionality reduction algorithms and the like. Various examples of specific algorithms include Bayesian Linear Regression, Boosted Decision Tree Regression, and Neural Network Regression, Back Propagation Neural Networks, the Apriori algorithm, K-Means Clustering, k-Nearest Neighbour (kNN), Learning Vector Quantization (LUQ), Self-Organizing Map (SOM), Locally Weighted Learning (LWL), Ridge Regression, Least Absolute Shrinkage and Selection Operator (LASSO), Elastic Net, and Least-Angle Regression (LARS), Principal Component Analysis (PCA) and Principal Component Regression (PCR).

Record management and reporting service 68G processes and responds to messages and queries received from computing devices 60 via interface layer 64. For example, record management and reporting service 68G may receive requests from client computing devices for event data related to individual workers, populations or sample sets of workers, geographic regions of environments 8 or environments 8 as a whole, individual or groups/types of PPEs 62. In response, record management and reporting service 68G accesses event information based on the request. Upon retrieving the event data, record management and reporting service 68G constructs an output response to the client application that initially requested the information. In some examples, the data may be included in a document, such as an HTML document, or the data may be encoded in a JSON format or presented by a dashboard application executing on the requesting client computing device. For instance, as further described in this disclosure, example user interfaces that include the event information are depicted in the figures.

As additional examples, record management and reporting service 68G may receive requests to find, analyze, and correlate PPE event information. For instance, record management and reporting service 68G may receive a query request from a client application for event data 74A over a historical time frame, such as a user can view PPE event information over a period of time and/or a computing device can analyze the PPE event information over the period of time.

In example implementations, services 68 may also include security service 68H that authenticate and authorize users and requests with PPEMS 6. Specifically, security service 68H may receive authentication requests from client applications and/or other services 68 to access data in data layer 72 and/or perform processing in application layer 66. An authentication request may include credentials, such as a username and password. Security service 68H may query security data 74A to determine whether the username and password combination is valid. Configuration data 74D may include security data in the form of authorization credentials, policies, and any other information for controlling access to PPEMS 6. As described above, security data 74A may include authorization credentials, such as combinations of valid usernames and passwords for authorized users of PPEMS 6. Other credentials may include device identifiers or device profiles that are allowed to access PPEMS 6.

Security service 68H may provide audit and logging functionality for operations performed at PPEMS 6. For instance, security service 68H may log operations performed by services 68 and/or data accessed by services 68 in data layer 72. Security service 68H may store audit information such as logged operations, accessed data, and rule processing results in audit data 74C. In some examples, security service 68H may generate events in response to one or more rules being satisfied. Security service 68H may store data indicating the events in audit data 74C.

In the example of FIG. 2, a safety manager may initially configure one or more safety rules. As such, remote user 24 may provide one or more user inputs at computing device 18 that configure a set of safety rules for work environment 8A and 8B. For instance, a computing device 60 of the safety manager may send a message that defines or specifies the safety rules. Such message may include data to select or create conditions and actions of the safety rules. PPEMS 6 may receive the message at interface layer 64 which forwards the message to rule configuration component 68I. Rule configuration component 68I may be combination of hardware and/or software that provides for rule configuration including, but not limited to: providing a user interface to specify conditions and actions of rules, receive, organize, store, and update rules included in safety rules data store 74E.

Safety rules data store 75E may be a data store that includes data representing one or more safety rules. Safety rules data store 74E may be any suitable data store such as a relational database system, online analytical processing database, object-oriented database, or any other type of data store. When rule configuration component 68I receives data defining safety rules from computing device 60 of the safety manager, rule configuration component 68I may store the safety rules in safety rules data store 75E.

In some examples, storing the safety rules may include associating a safety rule with context data, such that rule configuration component 68I may perform a lookup to select safety rules associated with matching context data. Context data may include any data describing or characterizing the properties or operation of a worker, worker environment, article of PPE, or any other entity. Context data of a worker may include, but is not limited to: a unique identifier of a worker, type of worker, role of worker, physiological or biometric properties of a worker, experience of a worker, training of a worker, time worked by a worker over a particular time interval, location of the worker, or any other data that describes or characterizes a worker. Context data of an article of PPE may include, but is not limited to: a unique identifier of the article of PPE; a type of PPE of the article of PPE; a usage time of the article of PPE over a particular time interval; a lifetime of the PPE; a component included within the article of PPE; a usage history across multiple users of the article of PPE; contaminants, hazards, or other physical conditions detected by the PPE, expiration date of the article of PPE; operating metrics of the article of PPE. Context data for a work environment may include, but is not limited to: a location of a work environment, a boundary or perimeter of a work environment, an area of a work environment, hazards within a work environment, physical conditions of a work environment, permits for a work environment, equipment within a work environment, owner of a work environment, responsible supervisor and/or safety manager for a work environment.

Table 4, shown below, includes a non-limiting set of rules that may be stored to safety rules data store 74E:

TABLE 4

SAFETY RULES

Hub shall immediately assert an "Attention Initial" Alert if Visor Position Status is OPEN in current location requiring Visor Open Allow = NO
Hub shall immediately assert a "Critical Initial" Alert if Filter Type Status is not equal to Filter Type or no filter found required by current location
Hub shall store all alerts in a queue.
Critical Alerts shall be highest priority in alert queue
Attention Alerts shall have secondary priority in alert queue
Hub shall immediately remove an alert from the queue if its conditions causing the alert have been corrected
A newly added alert to the alert queue shall be flagged as "Active", if it is higher priority than any other alarms in the queue.
A newly added alert to the alert queue shall be flagged as "Active", if all other alarms in the queue are Acknowledged or Notify
A newly added alert to the alert queue shall be flagged as "Pending" if an Active alert already exists in the queue and the newly added alert is lower in priority than the currently Active alert
If an Active alert in the queue is replaced by a new Active alert because of priority, the replaced alert shall be flagged as "Pending"
An active alert shall enable its respective haptic feedback and LED pattern
Hub shall assert an Acknowledge event when user presses and releases button within < 3 seconds. (Button_Tap)
Upon an Acknowledge event the Hub shall immediately flag the currently Active alert as Acknowledged, if any Active alerts are in the queue.
An Acknowledged alert shall disable its respective haptic feedback and LED pattern
Upon an Acknowledge event the Hub shall immediately flag the highest priority Pending alert as Active, if any Pending alerts exist in the queue.
Upon an Acknowledge event the Hub shall immediately flag the highest priority Acknowledged alert as Notify, if no Active alerts or Pending exist in the queue.
A Notify alert shall disable its respective haptic feedback and enable its LED pattern
Immediate Cloud Updates - Hub shall send safety violation asserted message via Wi-Fi to cloud service immediately upon assertion of alert
Immediate Worker Interface Updates - Hub shall send safety rule violation alerts asserted message via BLE to Worker Interface immediately upon assertion of alert
Immediate Cloud Updates - Hub shall send safety violation deasserted message via Wi-Fi to cloud service immediately upon deassertion of alert
Immediate Worker Interface Updates - Hub shall send safety violation deasserted message via BLE to Worker Interface immediately upon deassertion of alert It should be understood that the examples of Table 4 are provided for purposes of illustration only, and that other rules may be developed.

Figure 4:
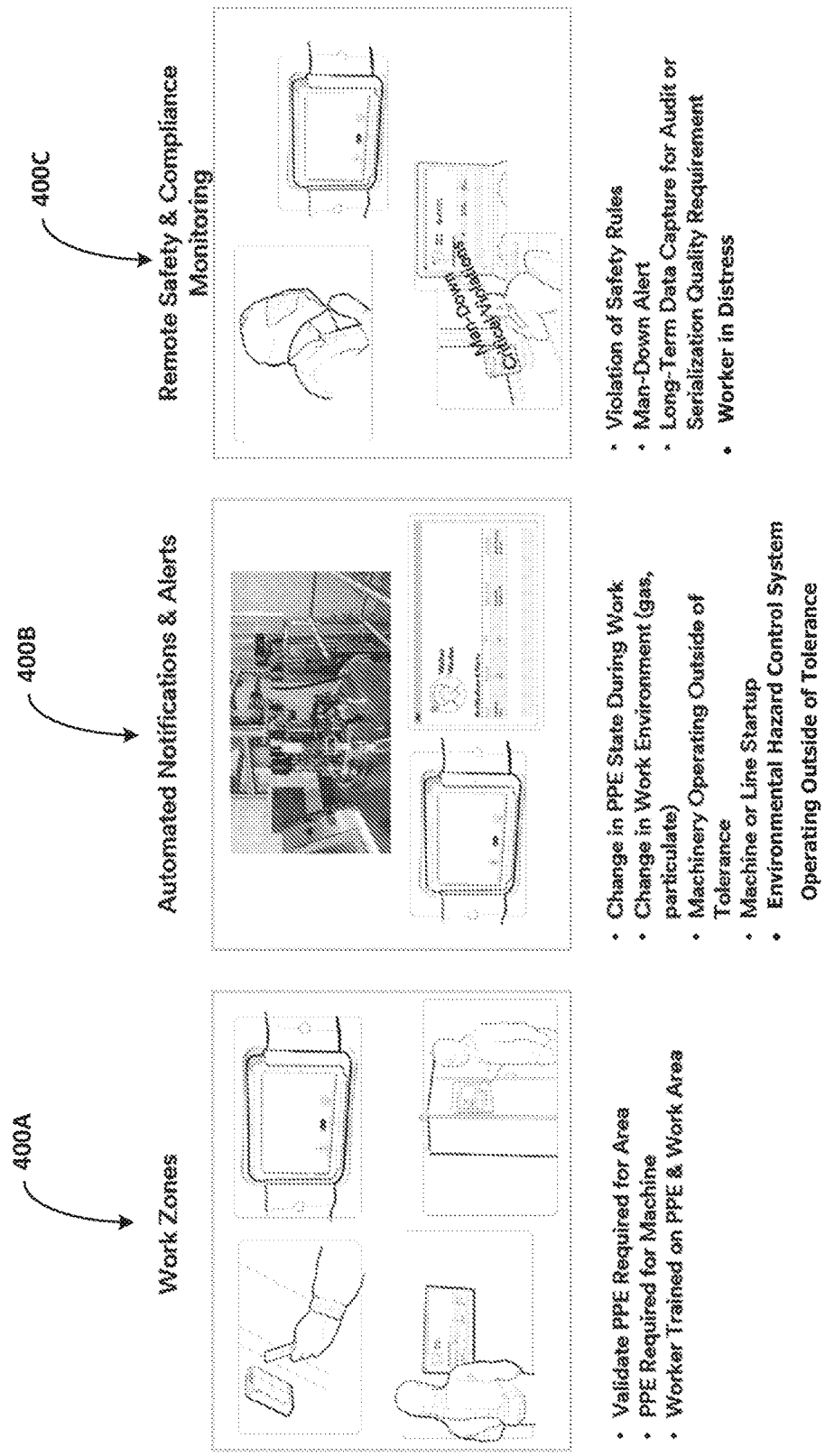
FIG. 4 illustrates one or more operations that may be performed by a computing device, in accordance with one or more techniques of this disclosure.

According to aspects of this disclosure, the rules may be used for purposes of reporting, to generate alerts, or the like. In an example for purposes of illustration, worker 10A may be equipped with respirator 13A and data hub 14A. Respirator 13A may include a filter to remove particulates but not organic vapors. Data hub 14A may be initially configured with and store a unique identifier of worker 10A. When initially assigning the respirator 13A and data hub to worker 10A, a computing device operated by worker 10A and/or a safety manager may cause RMRS 68G to store a mapping in work relation data 74F. Work relation data 74F may include mappings between data that corresponds to PPE, workers, and work environments. Work relation data 74F may be any suitable datastore for storing, retrieving, updating and deleting data. RMRS 69G may store a mapping between the unique identifier of worker 10A and a unique device identifier of data hub 14A. Work relation data store 74F may also map a worker to an environment. In the example of FIG. 4, self-check component 68I may receive or otherwise determine data from work relation data 74F for data hub 14A, worker 10A, and/or PPE associated with or assigned to worker 10A.

Worker 10A may initially put on respirator 13A and data hub 14A prior to entering environment 8A. As worker 10A approaches environment 8A and/or has entered environment 8A, data hub 14A may determine that worker 10A is within a threshold distance of entering environment 8A or has entered environment 8A. Data hub 14A may determine that it is within a threshold distance of entering environment 8A or has entered environment 8A and send a message that includes context data to PPEMS 6 that indicates data hub 14A is within a threshold distance of entering environment 8A.

According to aspects of this disclosure, as noted above, PPEMS 6 may additionally or alternatively apply analytics to predict the likelihood of a safety event. As noted above, a safety event may refer to activities of a worker 10 using PPE 62, a condition of PPE 62, or a hazardous environmental condition (e.g., that the likelihood of a safety event is relatively high, that the environment is dangerous, that SRL 11 is malfunctioning, that one or more components of SRL 11 need to be repaired or replaced, or the like). For example, PPEMS 6 may determine the likelihood of a safety event based on application of usage data from PPE 62 to historical data and models 74B. That is, PEMS 6 may apply historical data and models 74B to usage data from respirators 13 in order to compute assertions, such as anomalies or predicted occurrences of imminent safety events based on environmental conditions or behavior patterns of a worker using a respirator 13.

PPEMS 6 may apply analytics to identify relationships or correlations between sensed data from respirators 13, environmental conditions of environment in which respirators 13 are located, a geographic region in which respirators 13 are located, and/or other factors. PPEMS 6 may determine, based on the data acquired across populations of workers 10, which particular activities, possibly within certain environment or geographic region, lead to, or are predicted to lead to, unusually high occurrences of safety events. PPEMS 6 may generate alert data based on the analysis of the usage data and transmit the alert data to PPEs 62 and/or hubs 14.

Hence, according to aspects of this disclosure, PPEMS 6 may determine usage data of respirator 13, generate status indications, determine performance analytics, and/or perform prospective/preemptive actions based on a likelihood of a safety event.

For example, according to aspects of this disclosure, usage data from respirators 13 may be used to determine usage statistics. For example, PPEMS 6 may determine, based on usage data from respirators 13, a length of time that one or more components of respirator 13 (e.g., head top, blower, and/or filter) have been in use, an instantaneous velocity or acceleration of worker 10 (e.g., based on an accelerometer included in respirators 13 or hubs 14), a temperature of one or more components of respirator 13 and/or worker 10, a location of worker 10, a number of times or frequency with which a worker 10 has performed a self-check of respirator 13 or other PPE, a number of times or frequency with which a visor of respirator 13 has been opened or closed, a filter/cartridge consumption rate, fan/blower usage (e.g., time in use, speed, or the like), battery usage (e.g., charge cycles), or the like.

According to aspects of this disclosure, PPEMS 6 may use the usage data to characterize activity of worker 10. For example, PPEMS 6 may establish patterns of productive and nonproductive time (e.g., based on operation of respirator 13 and/or movement of worker 10), categorize worker movements, identify key motions, and/or infer occurrence of key events. That is, PPEMS 6 may obtain the usage data, analyze the usage data using services 68 (e.g., by comparing the usage data to data from known activities/events), and generate an output based on the analysis.

In some examples, the usage statistics may be used to determine when respirator 13 is in need of maintenance or replacement. For example, PPEMS 6 may compare the usage data to data indicative of normally operating respirators 13 in order to identify defects or anomalies. In other examples, PPEMS 6 may also compare the usage data to data indicative of a known service life statistics of respirators 13. The usage statistics may also be used to provide an understanding how respirators 13 are used by workers 10 to product developers in order to improve product designs and performance. In still other examples, the usage statistics may be used to gathering human performance metadata to develop product specifications. In still other examples, the usage statistics may be used as a competitive benchmarking tool. For example, usage data may be compared between customers of respirators 13 to evaluate metrics (e.g. productivity, compliance, or the like) between entire populations of workers outfitted with respirators 13.

Additionally or alternatively, according to aspects of this disclosure, usage data from respirators 13 may be used to determine status indications. For example, PPEMS 6 may determine that a visor of a respirator 13 is up in hazardous work area. PPEMS 6 may also determine that a worker 10 is fitted with improper equipment (e.g., an improper filter for a specified area), or that a worker 10 is present in a restricted/closed area. PPEMS 6 may also determine whether worker temperature exceeds a threshold, e.g., in order to prevent heat stress. PPEMS 6 may also determine when a worker 10 has experienced an impact, such as a fall.

Additionally or alternatively, according to aspects of this disclosure, usage data from respirators 13 may be used to assess performance of worker 10 wearing respirator 13. For example, PPEMS 6 may, based on usage data from respirators 13, recognize motion that may indicate a pending fall by worker 10 (e.g., via one or more accelerometers included in respirators 13 and/or hubs 14). In some instances, PPEMS 6 may, based on usage data from respirators 13, infer that a fall has occurred or that worker 10 is incapacitated. PPEMS 6 may also perform fall data analysis after a fall has occurred and/or determine temperature, humidity and other environmental conditions as they relate to the likelihood of safety events.

As another example, PPEMS 6 may, based on usage data from respirators 13, recognize motion that may indicate fatigue or impairment of worker 10. For example, PPEMS 6 may apply usage data from respirators 13 to a safety learning model that characterizes a motion of a user of at least one respirator. In this example, PPEMS 6 may determine that the motion of a worker 10 over a time period is anomalous for the worker 10 or a population of workers 10 using respirators 13.

Additionally or alternatively, according to aspects of this disclosure, usage data from respirators 13 may be used to determine alerts and/or actively control operation of respirators 13. For example, PPEMS 6 may determine that a safety event such as equipment failure, a fall, or the like is imminent. PPEMS 6 may send data to respirators 13 to change an operating condition of respirators 13. In an example for purposes of illustration, PPEMS 6 may apply usage data to a safety learning model that characterizes an expenditure of a filter of one of respirators 13. In this example, PPEMS 6 may determine that the expenditure is higher than an expected expenditure for an environment, e.g., based on conditions sensed in the environment, usage data gathered from other workers 10 in the environment, or the like. PPEMS 6 may generate and transmit an alert to worker 10 that indicates that worker 10 should leave the environment and/or active control of respirator 13. For example, PPEMS 6 may cause respirator to reduce a blower speed of a blower of respirator 13 in order to provide worker 10 with substantial time to exit the environment.

PPEMS 6 may generate, in some examples, a warning when worker 10 is near a hazard in one of environments 8 (e.g., based on location data gathered from a location sensor (GPS or the like) of respirators 13). PPEMS 6 may also applying usage data to a safety learning model that characterizes a temperature of worker 10. In this example, PPEMS 6 may determine that the temperature exceeds a temperature associated with safe activity over the time period and alert worker 10 to the potential for a safety event due to the temperature.

In another example, PPEMS 6 may schedule preventative maintenance or automatically purchase components for respirators 13 based on usage data. For example, PPEMS 6 may determine a number of hours a blower of a respirator 13 has been in operation, and schedule preventative maintenance of the blower based on such data. PPEMS 6 may automatically order a filter for respirator 13 based on historical and/or current usage data from the filter.

Again, PPEMS 6 may determine the above-described performance characteristics and/or generate the alert data based on application of the usage data to one or more safety learning models that characterizes activity of a user of one of respirators 13. The safety learning models may be trained based on historical data or known safety events. However, while the determinations are described with respect to PPEMS 6, as described in greater detail herein, one or more other computing devices, such as hubs 14 or respirators 13 may be configured to perform all or a subset of such functionality.

In some examples, a safety learning model is trained using supervised and/or reinforcement learning techniques. The safety learning model may be implemented using any number of models for supervised and/or reinforcement learning, such as but not limited to, an artificial neural networks, a decision tree, naïve Bayes network, support vector machine, or k-nearest neighbor model, to name only a few examples. In some examples, PPEMS 6 initially trains the safety learning model based on a training set of metrics and corresponding to safety events. The training set may include a set of feature vectors, where each feature in the feature vector represents a value for a particular metric. As further example description, PPEMS 6 may select a training set comprising a set of training instances, each training instance comprising an association between usage data and a safety event. The usage data may comprise one or more metrics that characterize at least one of a user, a work environment, or one or more articles of PPE. PPEMS 6 may, for each training instance in the training set, modify, based on particular usage data and a particular safety event of the training instance, the safety learning model to change a likelihood predicted by the safety learning model for the particular safety event in response to subsequent usage data applied to the safety learning model. In some examples, the training instances may be based on real-time or periodic data generated while PPEMS 6 managing data for one or more articles of PPE, workers, and/or work environments. As such, one or more training instances of the set of training instances may be generated from use of one or more articles of PPE after PPEMS 6 performs operations relating to the detection or prediction of a safety event for PPE, workers, and/or work environments that are currently in use, active, or in operation.

Some example metrics may include any characteristics or data described in this disclosure that relate to PPE, a worker, or a work environment, to name only a few examples. For instance, example metrics may include but are not limited to: worker identity, worker motion, worker location, worker age, worker experience, worker physiological parameters (e.g., heart rate, temperature, blood oxygen level, chemical compositions in blood, or any other measureable physiological parameter), or any other data descriptive of a worker or worker behavior. Example metrics may include but are not limited to: PPE type, PPE usage, PPE age, PPE operations, or any other data descriptive of PPE or PPE use. Example metrics may include but are not limited to: work environment type, work environment location, work environment temperature, work environment hazards, work environment size, or any other data descriptive of a work environment.

Each feature vector may also have a corresponding safety event. As described in this disclosure, a safety event may include but is not limited to: activities of a user of personal protective equipment (PPE), a condition of the PPE, or a hazardous environmental condition to name only a few examples. By training a safety learning model based on the training set, a safety learning model may be configured by PPEMS 6 to, when applying a particular feature vector to the safety learning model, generate higher probabilities or scores for safety events that correspond to training feature vectors that are more similar to the particular feature set. In the same way, the safety learning model may be configured by PPEMS 6 to, when applying a particular feature vector to the safety learning model, generate lower probabilities or scores for safety events that correspond to training feature vectors that are less similar to the particular feature set. Accordingly, the safety learning model may be trained, such that upon receiving a feature vector of metrics, the safety learning model may output one or more probabilities or scores that indicate likelihoods of safety events based on the feature vector. As such, PPEMS 6 may select likelihood of the occurrence as a highest likelihood of occurrence of a safety event in the set of likelihoods of safety events.

In some instances, PPEMS 6 may apply analytics for combinations of PPE. For example, PPEMS 6 may draw correlations between users of respirators 13 and/or the other PPE (such as fall protection equipment, head protection equipment, hearing protection equipment, or the like) that is used with respirators 13. That is, in some instances, PPEMS 6 may determine the likelihood of a safety event based not only on usage data from respirators 13, but also from usage data from other PPE being used with respirators 13. In such instances, PPEMS 6 may include one or more safety learning models that are constructed from data of known safety events from one or more devices other than respirators 13 that are in use with respirators 13.

In some examples, a safety learning model is based on safety events from one or more of a worker, article of PPE, and/or work environment having similar characteristics (e.g., of a same type). In some examples the "same type" may refer to identical but separate instances of PPE. In other examples the "same type" may not refer to identical instances of PPE. For instance, although not identical, a same type may refer to PPE in a same class or category of PPE, same model of PPE, or same set of one or more shared functional or physical characteristics, to name only a few examples. Similarly, a same type of work environment or worker may refer to identical but separate instances of work environment types or worker types. In other examples, although not identical, a same type may refer to a worker or work environment in a same class or category of worker or work environment or same set of one or more shared behavioral, physiological, environmental characteristics, to name only a few examples.

In some examples, to apply the usage data to a model, PPEMS 6 may generate a structure, such as a feature vector, in which the usage data is stored. The feature vector may include a set of values that correspond to metrics (e.g., characterizing PPE, worker, work environment, to name a few examples), where the set of values are included in the usage data. The model may receive the feature vector as input, and based on one or more relations defined by the model (e.g., probabilistic, deterministic or other functions within the knowledge of one of ordinary skill in the art) that has been trained, the model may output one or more probabilities or scores that indicate likelihoods of safety events based on the feature vector.

In general, while certain techniques or functions are described herein as being performed by certain components, e.g., PPEMS 6, respirators 13, or hubs 14, it should be understood that the techniques of this disclosure are not limited in this way. That is, certain techniques described herein may be performed by one or more of the components of the described systems. For example, in some instances, respirators 13 may have a relatively limited sensor set and/or processing power. In such instances, one of hubs 14 and/or PPEMS 6 may be responsible for most or all of the processing of usage data, determining the likelihood of a safety event, and the like. In other examples, respirators 13 and/or hubs 14 may have additional sensors, additional processing power, and/or additional memory, allowing for respirators 13 and/or hubs 14 to perform additional techniques. Determinations regarding which components are responsible for performing techniques may be based, for example, on processing costs, financial costs, power consumption, or the like.

As shown in FIG. 2, PPEMS 6 may include DFC 44D that performs the techniques described throughout this disclosure, such as in FIG. 1. In some examples, DFC 44D may interoperate with one or more components of PPEMS 6 to provide functionality resulting from the respective functionalities of DFC 44D and the one or more components of PPEMS 6.

Figure 3:
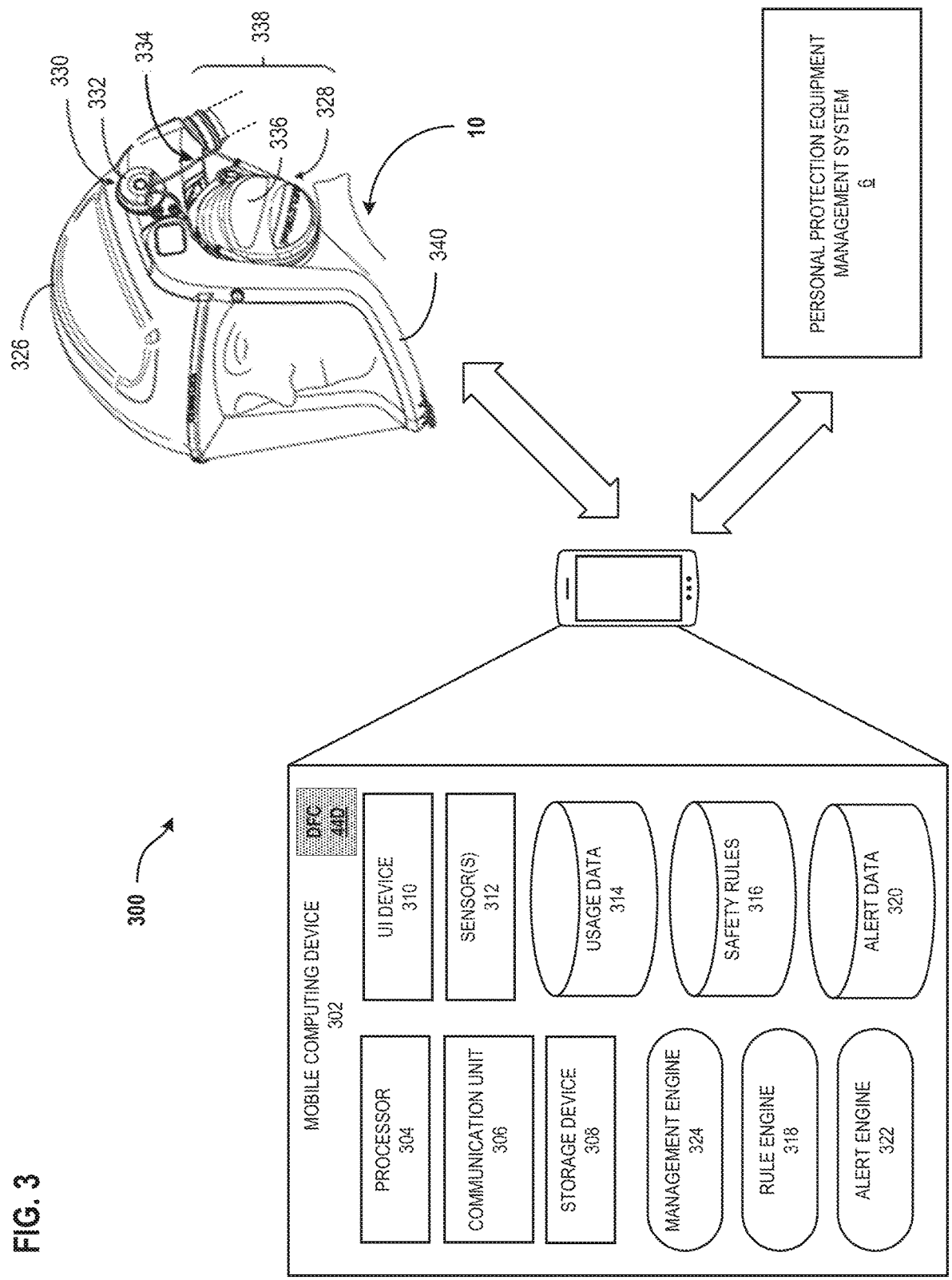
FIG. 3 illustrates an example system including a mobile computing device, a set of personal protective equipment communicatively coupled to the mobile computing device, and a personal protective equipment management system communicatively coupled to the mobile computing device, in accordance with techniques of this disclosure.

FIG. 3 illustrates an example system including a mobile computing device, a set of personal protective equipment communicatively coupled to the mobile computing device, and a personal protective equipment management system communicatively coupled to the mobile computing device, in accordance with techniques of this disclosure. For purposes of illustration only, system 300 includes mobile computing device 302, which may be an example of hub 14A in FIG. 1.

FIG. 3 illustrates components of mobile computing device 302 including processor 304, communication unit 306, storage device 308, user-interface (UI) device 310, sensors 312, usage data 314, safety rules 316, rule engine 318, alert data 320, alert engine 322, and management engine 324. As noted above, mobile computing device 302 represents one example of hubs 14 shown in FIG. 1. Many other examples of mobile computing device 302 may be used in other instances and may include a subset of the components included in example mobile computing device 302 or may include additional components not shown example mobile computing device 302 in FIG. 3.

In some examples, mobile computing device 302 may be an intrinsically safe computing device, smartphone, wrist- or head-wearable computing device, or any other computing device that may include a set, subset, or superset of functionality or components as shown in mobile computing device 302. Communication channels may interconnect each of the components in mobile computing device 302 for inter-component communications (physically, communicatively, and/or operatively). In some examples, communication channels may include a hardware bus, a network connection, one or more inter-process communication data structures, or any other components for communicating data between hardware and/or software.

Mobile computing device 302 may also include a power source, such as a battery, to provide power to components shown in mobile computing device 302. A rechargeable battery, such as a Lithium Ion battery, can provide a compact and long-life source of power. Mobile computing device 302 may be adapted to have electrical contacts exposed or accessible from the exterior of the hub to allow recharging the mobile computing device 302. As noted above, mobile computing device 302 may be portable such that it can be carried or worn by a user. Mobile computing device 302 can also be personal, such that it is used by an individual and communicates with personal protective equipment (PPE) assigned to that individual. In FIG. 3, mobile computing device 302 may be secured to a user by a strap. However, communication hub may be carried by a user or secured to a user in other ways, such as being secured to PPE being worn by the user, to other garments being worn to a user, being attached to a belt, band, buckle, clip or other attachment mechanism as will be apparent to one of skill in the art upon reading the present disclosure.

One or more processors 304 may implement functionality and/or execute instructions within mobile computing device 302. For example, processor 304 may receive and execute instructions stored by storage device 308. These instructions executed by processor 304 may cause mobile computing device 302 to store and/or modify information, within storage devices 308 during program execution. Processors 304 may execute instructions of components, such as rule engine 318 and alert engine 322 to perform one or more operations in accordance with techniques of this disclosure. That is, rule engine 318 and alert engine 322 may be operable by processor 304 to perform various functions described herein.

One or more communication units 306 of mobile computing device 302 may communicate with external devices by transmitting and/or receiving data. For example, mobile computing device 302 may use communication units 306 to transmit and/or receive radio signals on a radio network such as a cellular radio network. In some examples, communication units 306 may transmit and/or receive satellite signals on a satellite network such as a Global Positioning System (GPS) network. Examples of communication units 306 include a network interface card (e.g. such as an Ethernet card), an optical transceiver, a radio frequency transceiver, a GPS receiver, or any other type of device that can send and/or receive information. Other examples of communication units 306 may include Bluetooth®, GPS, 3G, 4G, and Wi-Fi® radios found in mobile devices as well as Universal Serial Bus (USB) controllers and the like.

One or more storage devices 308 within mobile computing device 302 may store information for processing during operation of mobile computing device 302. In some examples, storage device 308 is a temporary memory, meaning that a primary purpose of storage device 308 is not long-term storage. Storage device 308 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art.

Storage device 308 may, in some examples, also include one or more computer-readable storage media. Storage device 308 may be configured to store larger amounts of information than volatile memory. Storage device 308 may further be configured for long-term storage of information as non-volatile memory space and retain information after activate/off cycles. Examples of non-volatile memories include magnetic hard discs, optical discs, floppy discs, flash memories, or forms of electrically programmable memories (EPROM) or electrically erasable and programmable (EEPROM) memories. Storage device 308 may store program instructions and/or data associated with components such as rule engine 318 and alert engine 322.

UI device 310 may be configured to receive user input and/or output information to a user. One or more input components of UI device 310 may receive input. Examples of input are tactile, audio, kinetic, and optical input, to name only a few examples. UI device 310 of mobile computing device 302, in one example, include a mouse, keyboard, voice responsive system, video camera, buttons, control pad, microphone or any other type of device for detecting input from a human or machine. In some examples, UI device 310 may be a presence-sensitive input component, which may include a presence-sensitive screen, touch-sensitive screen, etc.

One or more output components of UI device 310 may generate output. Examples of output are data, tactile, audio, and video output. Output components of UI device 310, in some examples, include a presence-sensitive screen, sound card, video graphics adapter card, speaker, cathode ray tube (CRT) monitor, liquid crystal display (LCD), or any other type of device for generating output to a human or machine. Output components may include display components such as cathode ray tube (CRT) monitor, liquid crystal display (LCD), Light-Emitting Diode (LED) or any other type of device for generating tactile, audio, and/or visual output. Output components may be integrated with mobile computing device 302 in some examples.

UI device 310 may include a display, lights, buttons, keys (such as arrow or other indicator keys), and may be able to provide alerts to the user in a variety of ways, such as by sounding an alarm or vibrating. The user interface can be used for a variety of functions. For example, a user may be able to acknowledge or snooze an alert through the user interface. The user interface may also be used to control settings for the head top and/or turbo peripherals that are not immediately within the reach of the user. For example, the turbo may be worn on the lower back where the wearer cannot access the controls without significant difficulty.

Sensors 312 may include one or more sensors that generate data indicative of an activity of a worker 10 associated with mobile computing device 302 and/or data indicative of an environment in which mobile computing device 302 is located. Sensors 312 may include, as examples, one or more accelerometers, one or more sensors to detect conditions present in a particular environment (e.g., sensors for measuring temperature, humidity, particulate content, noise levels, air quality, or any variety of other characteristics of environments in which respirator 13 may be used), or a variety of other sensors.

Mobile computing device 302 may store usage data 314 from components of respirator 13N. For example, as described herein, components of respirator 13N (or any other examples of respirators 13) may generate data regarding operation of system 100 that is indicative of activities of worker 10 and transmit the data in real-time or near real-time to mobile computing device 302.

In some examples, mobile computing device 302 may immediately relay usage data 314 to another computing device, such as PPEMS 6, via communication unit 306. In other examples, storage device 308 may store usage data 314 for some time prior to uploading the data to another device. For example, in some instances, communication unit 306 may be able to communicate with system 100 but may not have network connectivity, e.g., due to an environment in which system 100 is located and/or network outages. In such instances, mobile computing device 302 may store usage data 314 to storage device 308, which may allow the usage data to be uploaded to another device upon a network connection becoming available. Mobile computing device 302 may store safety rules 316 as described in this disclosure. Safety rules 316 may be stored in any suitable data store as described in this disclosure.

System 300 may include head top 326 and hearing protector 328, in accordance with this disclosure. As shown in FIG. 3, head top 326 may include structure and functionality that is similar to or the same as respirator 13A as described in FIG. 1 and other embodiments of this disclosures. Head top 326 (or other headworn device, such as a head band) may include hearing protector 328 that includes, ear muff attachment assembly 330. Ear muff attachment assembly 330 may include housing 332, an arm set 334, and ear muffs 336. Hearing protector 328 may include two separate ear muff cups 336, one of which is visible in FIG. 3 and the other on the opposite side of the user's head and similarly configured to the visible ear muff cup in FIG. 3. Arm set 334 is rotatable between one or more different positions, such that hearing protector 328 may be adjusted and/or toggled, for example, between "active" and "standby" positions (or one or more additional intermediate positions). In an active position, hearing protector 328 is configured to at least partially cover a user's ear. In a standby mode, hearing protector 328 is in a raised position away from and/or out of contact with a user's head. A user is able to switch between active and standby positions when entering or leaving an area necessitating hearing protection, for example, or as may be desired by the user. Adjustment to a standby position allows hearing protector 328 to be readily available for the user to move hearing protector 328 into an active position in which hearing protection is provided without the need to carry or store ear muffs.

Ear muff attachment assembly 330 may be attached directly or indirectly to a helmet, hard hat, strap, head band, or other head support, such as a head top 326. Head top 326 may be worn simultaneously with, and provide a support for, ear muff attachment assembly 330. Ear muff attachment assembly 330 is attached to an outer surface of head top 326, and arm set 334 extends generally downwardly around an edge of head top 326 such that ear muffs of hearing protector 328 may be desirably positioned to cover a user's ear.

In various examples, head top 326 and ear muff attachment assembly 330 may be joined using various suitable attachment components, such as snap-fit components, rivets, mechanical fasteners, adhesive, or other suitable attachment components as known in the art. Ear muffs of hearing protector 328 are configured to cover at least a portion of a user's ear and/or head. In FIG. 3, ear muffs exhibit a cup shape and include a cushion and a sound absorber (not shown). Cushions are configured to contact a user's head and/or ear when ear muffs are in an active position forming an appropriate seal to prevent sound waves from entering. Arm set 334 extends outwardly from head top 326 and is configured to carry ear muffs of hearing protector 328.

In the example of FIG. 3, ear muff attachment assembly 330 may have positional or motion sensors to detect whether the ear muffs are in the standby or active position. The positional or motion sensor may generate one or more signals that indicate a particular position from a set of one or more positions. The signals may indicate one or more position values (e.g., discrete "active"/"standby" values, numeric position representations, or any other suitable encoding or measurement values). If, for example, the standby condition is detected by the one or more positional or motion sensors and if an environmental sound detector detects unsafe sound levels, then a computing device may generate an indication of output, such as a notification, log entry, or other type of output. In some examples, the indication of output may be audible, visual, haptic, or any other physical sensory output.

In high noise environment workers may be required to use hearing protection in the form of ear plugs or ear muffs. Ear muffs typically comprise cup shaped shell with a sound absorbing liner that seals against the ear of the user. Many workers also use head and/or face protection while wearing ear muffs. Therefore, many ear muff models are designed to attach to a helmet, hard hat or other headgear, such as shown in FIG. 3. The ear muffs may be affixed to the headgear via an arm that attaches to the headgear and is adjustable between various positions over or away from the worker's ear.

As described above, headgear mounted ear muffs rotate between two positions: the active position where the ear muffs cover the worker's ears providing hearing protection, and the standby position where the ear muffs are rotated up and away from the ears. While in the standby position the ear muff does not provide hearing protection to the worker. In some types of headgear attached ear muffs, the muffs can be pivoted outward away from the ear of the user in the standby position. In this case, the ear muffs rest at a small distance away from the head of the user. In the active position, the muffs are pivoted toward the head where it is sealed around the ears of the user providing hearing protection.

Returning to mobile computing device 302, safety rules 316 may include threshold information both for a length of time visor 340 is allowed to be in an open position before an alert is generated, and the level or type of contaminants that will trigger an alert. For example, when mobile computing device 302 receives information from an environmental beacon that there are no hazards present in the environment, the threshold for the visor 340 being in the open position may be infinite. If a hazard is present in the environment, then the threshold may be determined based upon the concern of the threat to the user. Radiation, dangerous gases, or toxic fumes would all require assignment of the threshold to be on the order of one second or less.

Thresholds for head top temperature can be used to predict, e.g., by PPEMS 6, heat related illness and more frequent hydration and/or rest periods can be recommended to the user. Thresholds can be used for predicted battery run time. As the battery nears selectable remaining run time, the user can be notified/warned to complete their current task and seek a fresh battery. When a threshold is exceeded for a specific environmental hazard, an urgent alert can be given to the user to evacuate the immediate area. Thresholds can be customized to various levels of openness for the visor. In other words, a threshold for the amount of a time the visor may be open without triggering an alarm may be longer if the visor is in the partially open position as compared to the open position.

Reaching different thresholds set forth in safety rules 316 may result in triggering different types of alerts or alarms. For example, alarms may be informational (not requiring a user response), urgent (repeated and requiring a response or acknowledgement from a user), or emergency (requiring immediate action from a user.) The type of alert or alarm can be tailored to the environment. Different types of alerts and alarms can be coupled together to get user attention. In some instances, a user may be able to "snooze" an alert or alarm.

Rule engine 318 may be a combination of hardware and software that executes one or more safety rules, such as safety rules 316. For instance, rule engine 318 may determine which safety rules to execute based on context data, information included in the safety rule set, other information received from PPEMS 6 or other computing devices, user input from the worker, or any other source of data that indicates which safety rules to execute. In some examples, safety rules 316 may be installed prior to a worker entering a work environment, while in other examples, safety rules 316 be dynamically retrieved by mobile computing device 302 based on context data generated at first particular point in time.

Rule engine 318 may execute safety rules periodically, continuously, or asynchronously. For instance, rule engine 318 may execute safety rules periodically by evaluating the conditions of such rules each time a particular time interval passes or expires (e.g., every second, every minute, etc.). In some examples, rule engine 318 may execute safety rules continuously by checking such conditions using one or more scheduling techniques that continuously evaluate the conditions of such rules. In some examples, rule engine 318 may execute safety rules asynchronously, such as in response to detecting an event. An event may be any detectable occurrence, such as moving to a new location, detecting a worker, coming within a threshold distance of another object, or any other detectable occurrence.

Rule engine 318, upon determining that a condition of a safety rule has or has not been satisfied may perform one or more actions associated with the safety rule by executing one or more operations that define the actions. For instance, rule engine 318 may execute a condition that determines if a worker is approaching or has entered a work environment, (a) whether a PAPR is being worn by the worker and (b) whether the filter in the PAPR of a particular type of filter, e.g., a filter that removes contaminants of a particular type. This safety rule may specify actions if the condition is not satisfied which cause rule engine 318 to generate an alert at mobile computing device 302 using UI device 310 and send a message using communication unit 306 to PPEMS 6, which may cause PPEMS 6 to send a notification to a remote user (e.g., the safety manager).

Alert data 320 may be used for generating alerts for output by UI device 310. For example, mobile computing device 302 may receive alert data from PPEMS 6, end-user computing devices 16, remote users using computing devices 18, safety stations 15, or other computing devices as illustrated in FIG. 1. In some examples, alert data 320 may be based on operation of system 300. For example, mobile computing device 302 may receive alert data 320 that indicates a status of system 300, that system 300 is appropriate for the environment in which system 300 is located, that the environment in which system 300 is located is unsafe, or the like.

In some examples, additionally or alternatively, mobile computing device 302 may receive alert data 320 associated with a likelihood of a safety event. For example, as noted above, PPEMS 6 may, in some examples, apply historical data and models to usage data from system 300 in order to compute assertions, such as anomalies or predicted occurrences of imminent safety events based on environmental conditions or behavior patterns of a worker using system 300. That is, PPEMS 6 may apply analytics to identify relationships or correlations between sensed data from system 300, environmental conditions of environment in which system 300 is located, a geographic region in which system 300 is located, and/or other factors. PPEMS 6 may determine, based on the data acquired across populations of workers 10, which particular activities, possibly within certain environment or geographic region, lead to, or are predicted to lead to, unusually high occurrences of safety events. Mobile computing device 302 may receive alert data 320 from PPEMS 6 that indicates a relatively high likelihood of a safety event.

Alert engine 322 may be a combination of hardware and software that interprets alert data 320 and generate an output at UI device 310 (e.g., an audible, visual, or tactile output) to notify worker 10 of the alert condition (e.g., that the likelihood of a safety event is relatively high, that the environment is dangerous, that system 300 is malfunctioning, that one or more components of system 300 need to be repaired or replaced, or the like). In some instances, alert engine 322 may also interpret alert data 320 and issue one or more commands to system 300 to modify operation or enforce rules of system 300 in order to bring operation of system 300 into compliance with desired/less risky behavior. For example, alert engine 322 may issue commands that control the operation of head top 326 or a clean air supply source.

As shown in FIG. 3, mobile computing device 302 may include DFC 44D that performs the techniques described throughout this disclosure, such as in FIG. 1. In some examples, DFC 44D may interoperate with one or more components mobile computing device 302 to provide functionality resulting from the respective functionalities of DFC 44D and the one or more components of mobile computing device 302.

FIG. 4 illustrates one or more operations that may be performed by a computing device, in accordance with one or more techniques of this disclosure. In a workzone 400A, a computing device implementing a DFC may determine whether certain PPE is required for a work area based on information from an industrial control device, environmental monitor, and or PPE. In workzone 400A the computing device may determine whether PPE is required for the industrial controller device or the industrial device. In some examples, the computing device may determine whether the worker is trained to use PPE, the industrial device, the industrial controller device, and/or operate in in workzone 400A.

In some examples, a computing device implementing a DFC may generate for output one or more notifications and/or alerts. For instance, the computing device may generate an output in response to a change in PPE state. In some examples, the computing device may generate an output in response to a change in a worker environment (e.g., gases or other particulate levels). In some examples, the computing device may generate an output in response to detecting an industrial device or industrial controller device in response to operation outside of one or more preset (or safe) limits. In some examples, the computing device may generate an output in response to an industrial device and/or industrial controller device starting or stopping operation.

In some examples, a computing device implementing a DFC may perform remote safety and/or compliance monitoring. The computing device may determine a violation of one or more safety rules. In some examples, the computing device may determine if a person has fallen (e.g., "man down" event). In some examples, the computing device may capture, log, and/or analyze data from PPE, work environment, industrial controller device, and/or industrial controller to perform audits for compliance and/or serialization quality requirements.

Figure 5:
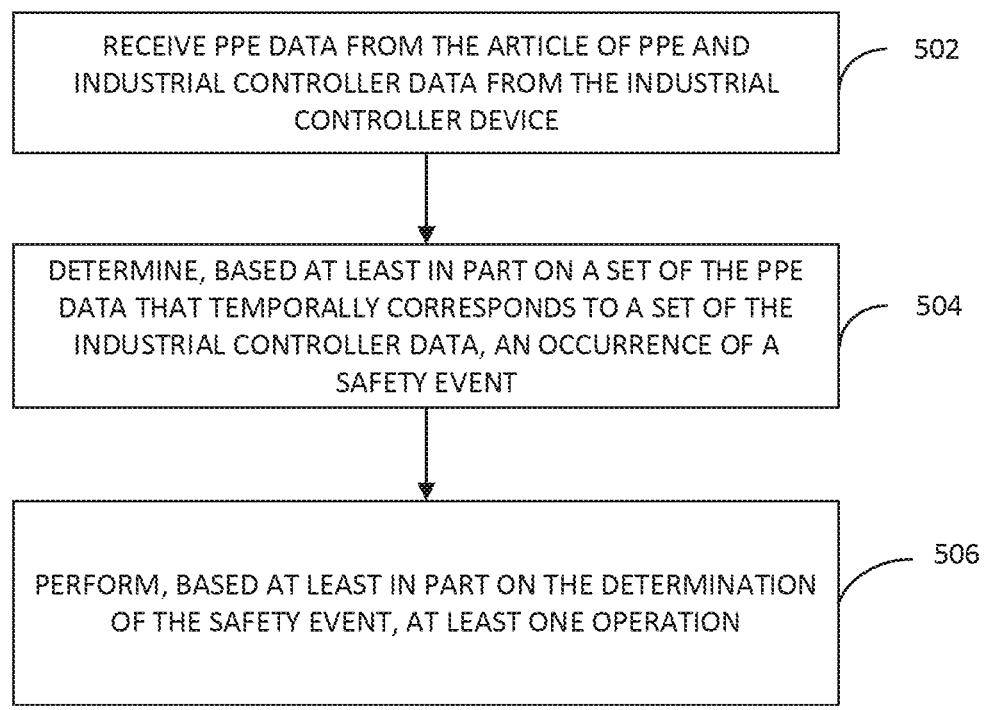
FIG. 5 illustrates example operations that may be performed by one or more computing devices in accordance with techniques of this disclosure.

FIG. 5 illustrates example operations that may be performed by one or more computing devices in accordance with techniques of this disclosure. The example operations may be performed by one or more DFC's implemented at one or more computing devices illustrated in FIG. 1. For example, DFC 44D may receive PPE data from an article of PPE and industrial controller data from an industrial controller device (503). DFC 44D may determine, based at least in part on a set of the PPE data that temporally corresponds to a set of the industrial controller data, an occurrence of a safety event (504). DFC 44D may perform, based at least in part on the determination of the safety event, at least one operation. For example, DFC 44D may generate an alert for the worker. DFC 44D may send one or more messages to control device 42, industrial device 40 and/or PPEMS 6 based on the determination of the safety event.

In the present detailed description of the preferred embodiments, reference is made to the accompanying drawings, which illustrate specific embodiments in which the invention may be practiced. The illustrated embodiments are not intended to be exhaustive of all embodiments according to the invention. It is to be understood that other embodiments may be utilized and structural or logical changes may be made without departing from the scope of the present invention. The following detailed description, therefore, is not to be taken in a limiting sense, and the scope of the present invention is defined by the appended claims.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein.

As used in this specification and the appended claims, the singular forms "a," "an," and "the" encompass embodiments having plural referents, unless the content clearly dictates otherwise. As used in this specification and the appended claims, the term "or" is generally employed in its sense including "and/or" unless the content clearly dictates otherwise.

Spatially related terms, including but not limited to, "proximate," "distal," "lower," "upper," "beneath," "below," "above," and "on top," if used herein, are utilized for ease of description to describe spatial relationships of an element(s) to another. Such spatially related terms encompass different orientations of the device in use or operation in addition to the particular orientations depicted in the figures and described herein. For example, if an object depicted in the figures is turned over or flipped over, portions previously described as below or beneath other elements would then be above or on top of those other elements.

As used herein, when an element, component, or layer for example is described as forming a "coincident interface" with, or being "on," "connected to," "coupled with," "stacked on" or "in contact with" another element, component, or layer, it can be directly on, directly connected to, directly coupled with, directly stacked on, in direct contact with, or intervening elements, components or layers may be on, connected, coupled or in contact with the particular element, component, or layer, for example. When an element, component, or layer for example is referred to as being "directly on," "directly connected to," "directly coupled with," or "directly in contact with" another element, there are no intervening elements, components or layers for example. The techniques of this disclosure may be implemented in a wide variety of computer devices, such as servers, laptop computers, desktop computers, notebook computers, tablet computers, hand-held computers, smart phones, and the like. Any components, modules or units have been described to emphasize functional aspects and do not necessarily require realization by different hardware units. The techniques described herein may also be implemented in hardware, software, firmware, or any combination thereof. Any features described as modules, units or components may be implemented together in an integrated logic device or separately as discrete but interoperable logic devices. In some cases, various features may be implemented as an integrated circuit device, such as an integrated circuit chip or chipset. Additionally, although a number of distinct modules have been described throughout this description, many of which perform unique functions, all the functions of all of the modules may be combined into a single module, or even split into further additional modules. The modules described herein are only exemplary and have been described as such for better ease of understanding.

If implemented in software, the techniques may be realized at least in part by a computer-readable medium comprising instructions that, when executed in a processor, performs one or more of the methods described above. The computer-readable medium may comprise a tangible computer-readable storage medium and may form part of a computer program product, which may include packaging materials. The computer-readable storage medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The computer-readable storage medium may also comprise a non-volatile storage device, such as a hard-disk, magnetic tape, a compact disk (CD), digital versatile disk (DVD), Blu-ray disk, holographic data storage media, or other non-volatile storage device.

The term "processor," as used herein may refer to any of the foregoing structure or any other structure suitable for implementation of the techniques described herein. In addition, in some aspects, the functionality described herein may be provided within dedicated software modules or hardware modules configured for performing the techniques of this disclosure. Even if implemented in software, the techniques may use hardware such as a processor to execute the software, and a memory to store the software. In any such cases, the computers described herein may define a specific machine that is capable of executing the specific functions described herein. Also, the techniques could be fully implemented in one or more circuits or logic elements, which could also be considered a processor.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media, which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor", as used may refer to any of the foregoing structure or any other structure suitable for implementation of the techniques described. In addition, in some aspects, the functionality described may be provided within dedicated hardware and/or software modules. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

It is to be recognized that depending on the example, certain acts or events of any of the methods described herein can be performed in a different sequence, may be added, merged, or left out all together (e.g., not all described acts or events are necessary for the practice of the method). Moreover, in certain examples, acts or events may be performed concurrently, e.g., through multi-threaded processing, interrupt processing, or multiple processors, rather than sequentially.

In some examples, a computer-readable storage medium includes a non-transitory medium. The term "non-transitory" indicates, in some examples, that the storage medium is not embodied in a carrier wave or a propagated signal. In certain examples, a non-transitory storage medium stores data that can, over time, change (e.g., in RAM or cache).

Various examples have been described. These and other examples are within the scope of the following claims.

What is claimed is:

1. A system comprising:
an article of personal protective equipment (PPE) that includes a communication component;
an industrial controller device that is configured to control an industrial device and includes a communication component; and
a computing device communicatively coupled to the article of PPE and the industrial controller device, wherein the computing device comprises:
one or more computer processors; and
a memory comprising instructions that when executed by the one or more computer processors cause the one or more computer processors to:
receive PPE data from the article of PPE and industrial controller data from the industrial controller device;
determine, based at least in part on a set of the PPE data that temporally corresponds to a set of the industrial controller data, an occurrence of a safety event; and
perform, based at least in part on the determination of the safety event, at least one operation.

2. The system of claim 1, wherein the memory comprises instructions that when executed cause the one or more computer processors to:
- select, from the set of PPE data, at least one PPE identifier that corresponds to the article of PPE;
- select, from the set of industrial controller data that corresponds to the industrial controller device, at least one industrial controller identifier that corresponds to the industrial controller; and
- determine the safety event based at least in part on a determination, using the PPE identifier and the industrial controller identifier, by the computing device that an inspection history of the industrial controller device or the article of PPE does not satisfy at least one of a threshold or a rule that is configured for the industrial controller device or the article of PPE.

3. The system of claim 2, wherein the threshold or the safety rule is based at least in part on one of a particular timestamp or a period of time.

* * * * *